United States Patent
Kotsianis et al.

(10) Patent No.: US 9,249,081 B2
(45) Date of Patent: Feb. 2, 2016

(54) PROCESSES FOR THE PRODUCTION OF ACRYLIC ACIDS AND ACRYLATES

(75) Inventors: Ilias S. Kotsianis, Houston, TX (US); Sean Mueller, Pasadena, TX (US); Dick Nagaki, The Woodlands, TX (US); Tianshu Pan, Houston, TX (US); Craig J. Peterson, Houston, TX (US); Josefina T. Chapman, Houston, TX (US)

(73) Assignee: Celanese International Corporation, Irving, TX (US)

( * ) Notice: Subject to any disclaimer, the term of this patent is extended or adjusted under 35 U.S.C. 154(b) by 1049 days.

(21) Appl. No.: 13/328,231

(22) Filed: Dec. 16, 2011

(65) Prior Publication Data

US 2013/0158295 A1     Jun. 20, 2013

(51) Int. Cl.
*C07C 51/42*  (2006.01)
*C07C 51/44*  (2006.01)

(52) U.S. Cl.
CPC ............... *C07C 51/42* (2013.01); *C07C 51/44* (2013.01)

(58) Field of Classification Search
CPC .............................. C07C 51/42; C07C 51/44
See application file for complete search history.

(56) References Cited

U.S. PATENT DOCUMENTS

| | | | |
|---|---|---|---|
| 3,436,423 A * | 4/1969 | Ackermann | 568/457 |
| 3,689,541 A * | 9/1972 | Sennewald et al. | 562/600 |
| 4,040,913 A * | 8/1977 | Clovis et al. | 562/598 |
| 4,599,144 A * | 7/1986 | Baleiko et al. | 203/15 |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,364,824 A | 11/1994 | Andrews et al. | |
| RE35,377 E | 11/1996 | Steinberg et al. | |
| 5,599,976 A | 2/1997 | Scates et al. | |
| 5,821,111 A | 10/1998 | Grady et al. | |
| 5,831,224 A | 11/1998 | Wattles et al. | |
| 6,132,555 A | 10/2000 | Rikkinen et al. | |
| 6,143,930 A | 11/2000 | Singh et al. | |
| 6,232,352 B1 * | 5/2001 | Vidalin | 518/700 |
| 6,478,929 B1 * | 11/2002 | Parten | 203/17 |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 7,005,541 B2 | 2/2006 | Cheung et al. | |
| 7,115,772 B2 | 10/2006 | Picard et al. | |
| 7,208,624 B2 | 4/2007 | Scates et al. | |
| 7,803,969 B2 | 9/2010 | Nordhoff et al. | |
| 2007/0293689 A1 * | 12/2007 | Siegert et al. | 549/368 |

OTHER PUBLICATIONS

Ott et al. Chem. End. Proc. 2005, 44, 687-694.*
Ai, M. J. Catal., 1987, 107, 201-208.*
Piret et al. Ind. Eng. Chem. 1949, 40, 661-672.*
M. Ai, J. Catal., 107, 201, (1987).

(Continued)

*Primary Examiner* — Matthew Coughlin

(57) ABSTRACT

In one embodiment, the invention is to a process for producing an acrylate product. The process comprises the step of dehydrating a crude alkylenating agent stream to form a dehydrated alkylenating agent stream and a water stream. The process further comprises reacting acetic acid with at least a portion of the dehydrated alkylenating agent stream to form a crude acrylate product stream comprising acrylate product and alkylenating agent stream. The dehydrating of the crude alkylenating stream is accomplished using at least one evaporator or at least one distillation column.

29 Claims, 5 Drawing Sheets

(56) References Cited

OTHER PUBLICATIONS

M. Ai., J. Catal., 124, 293, (1990).
M. Ai., Appl. Catal., 36, 221, (1988).
M. Ai., Shokubai, 29, 522, (1987).
International Search Report and Written Opinion mailed Jan. 31, 2013 in corresponding International Application No. PCT/US2012/068893.

* cited by examiner

PROCESSES FOR THE PRODUCTION OF ACRYLIC ACIDS AND ACRYLATES

FIELD OF THE INVENTION

The present invention relates generally to the production of acrylic acid via the condensation of acetic acid and formaldehyde. More specifically, the present invention relates to the removal of water from the formaldehyde feed material prior to the condensation reaction.

BACKGROUND OF THE INVENTION

α,β-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process utilizes: (1) the reaction of acetylene with water and carbon monoxide; and/or (2) the reaction of an alcohol and carbon monoxide, in the presence of an acid, e.g., hydrochloric acid, and nickel tetracarbonyl, to yield a crude product comprising the acrylate ester as well as hydrogen and nickel chloride. Another conventional process involves the reaction of ketene (often obtained by the pyrolysis of acetone or acetic acid) with formaldehyde, which yields a crude product comprising acrylic acid and either water (when acetic acid is used as a pyrolysis reactant) or methane (when acetone is used as a pyrolysis reactant). These processes have become obsolete for economic, environmental, or other reasons.

More recent acrylic acid production processes have relied on the gas phase oxidation of propylene, via acrolein, to form acrylic acid. The reaction can be carried out in single- or two-step processes but the latter is favored because of higher yields. The oxidation of propylene produces acrolein, acrylic acid, acetaldehyde and carbon oxides. Acrylic acid from the primary oxidation can be recovered while the acrolein is fed to a second step to yield the crude acrylic acid product, which comprises acrylic acid, water, small amounts of acetic acid, as well as impurities such as furfural, acrolein, and propionic acid. Purification of the crude product may be carried out by azeotropic distillation. Although this process may show some improvement over earlier processes, this process suffers from production and/or separation inefficiencies. In addition, this oxidation reaction is highly exothermic and, as such, creates an explosion risk. As a result, more expensive reactor design and metallurgy are required. Also, the cost of propylene is often prohibitive.

The aldol condensation reaction of formaldehyde and acetic acid and/or carboxylic acid esters has been disclosed in literature. This reaction forms acrylic acid and is often conducted over a catalyst. For example, condensation catalysts consisting of mixed oxides of vanadium and phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987). The acetic acid conversions in these reactions, however, may leave room for improvement. Although this reaction is disclosed, there has been little if any disclosure relating to: 1) separation schemes that may be employed to effectively provide purified acrylic acid from the aldol condensation crude product; or 2) treatment of the reactants to improve reaction efficiency.

Formalin is typically employed as a source of the formaldehyde that is used as a reactant in the aldol condensation reaction. Formalin usually contains between 37 wt. % to 55 wt. % formaldehyde, 44 wt. % to 60 wt. % water, and a small amount of methanol. In addition, water is formed as a by-product during the aldol condensation reaction of formaldehyde and acetic acid. Thus, the resulting crude acrylic acid product contains a significant portion of water and it is necessary to remove same in order to recover a purified acrylic acid product. Also, the higher amounts of water are believed to negatively affect the stability and/or lifetime of the condensation catalyst.

Thus, the need exists for energy efficient processes for producing purified acrylic acid, which provide improved separation efficiencies and improved catalyst stability and/or lifetime.

The references mentioned above are hereby incorporated by reference.

BRIEF DESCRIPTION OF DRAWINGS

The invention is described in detail below with reference to the appended drawings, wherein like numerals designate similar parts.

SUMMARY OF THE INVENTION

Figure 1:
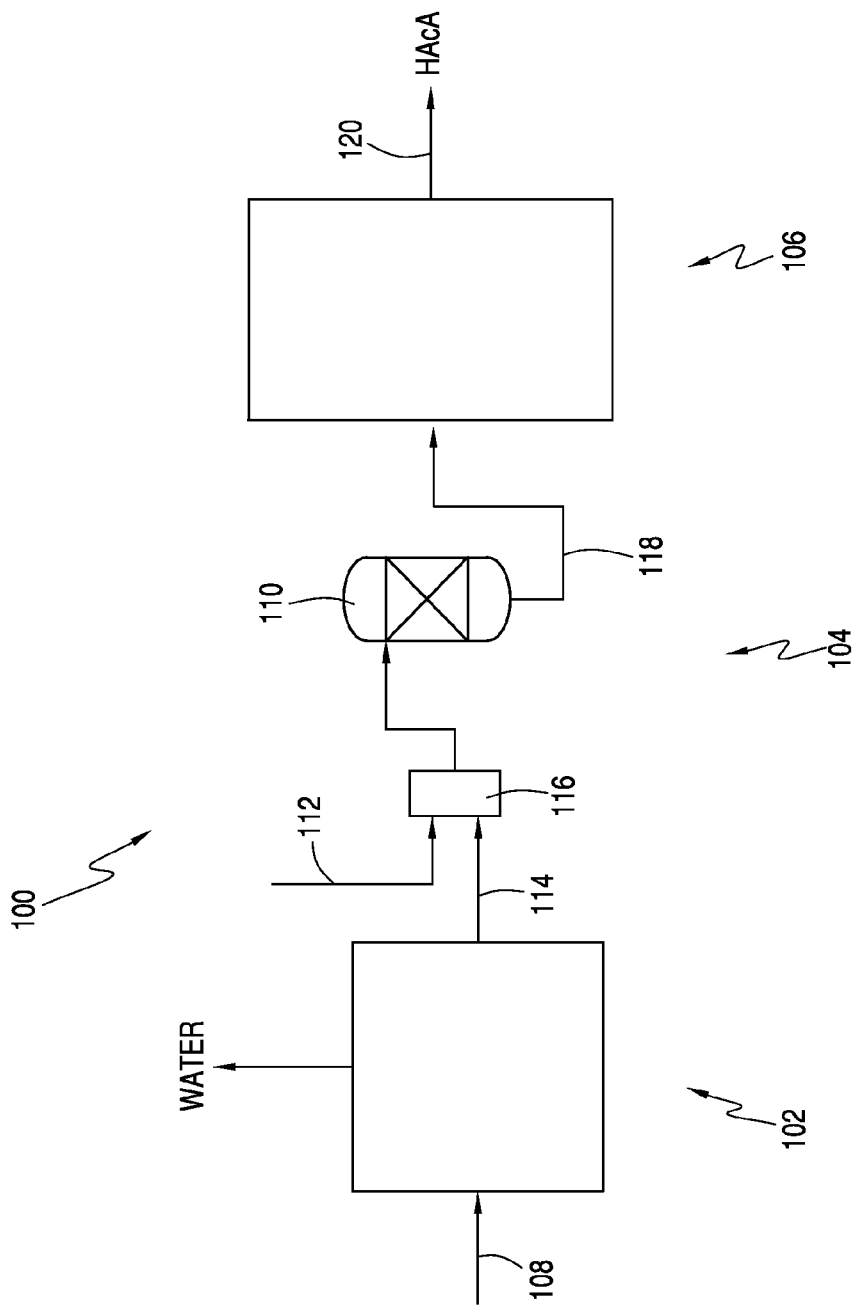
FIG. 1 is a process flowsheet showing an acrylic acid reaction/separation system in accordance with an embodiment of the present invention.

In one embodiment, the invention is to a process for producing an acrylate product. The process comprises the steps of dehydrating a crude alkylenating agent stream comprising alkylenating agent and water to form a dehydrated alkylenating agent stream and a water stream; reacting acetic acid with at least a portion of the dehydrated alkylenating agent stream to form a crude acylate product stream comprising acrylate product and alkylenating agent; and recovering the acrylate product.

In another embodiment, the inventive process for producing an acrylate product comprises the steps of reacting a dehydrated alkylenating agent stream with acetic acid from an acetic acid feed stream in a reactor to form a crude acrylate product stream comprising the acrylate product, an alkylenating agent and acetic acid; and recovering the acrylate product.

In another embodiment, the inventive process for producing an acrylate product comprises the steps of dehydrating a crude alkylenating stream to form a dehydrated crude alkylenating stream having at least 55 wt. % alkylenating agent; reacting the dehydrated alkylenating stream with acetic acid from an acetic acid feed stream in a reactor to form a crude acrylate product stream comprising the acrylate product, an alkylenating agent and acetic acid; and recovering the acrylate product.

In another embodiment, the inventive process for producing an acrylate product comprises the step of dehydrating a crude alkylenating stream to achieve at least 60 wt. % formaldehyde in the dehydrated stream; reacting the dehydrated alkylenating stream with acetic acid from an acetic acid feed stream in a reactor to form a crude acrylate product stream comprising the acrylate product, an alkylenating agent and acetic acid; and recovering the acrylate product.

In another embodiment, the inventive process for producing an acrylate product comprises the steps of dehydrating a crude alkylenating stream to remove at least 15% of the water therefrom; reacting the dehydrated alkylenating stream with acetic acid from an acetic acid feed stream in a reactor to form a crude acrylate product stream comprising the acrylate product, an alkylenating agent and acetic acid; and recovering the acrylate product.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. In the interest of finding a new reaction path, the aldol condensation reaction of acetic acid and an alkylenating agent, e.g., formaldehyde, has been investigated. This reaction may yield a unique crude product that comprises, inter alia, a higher amount of (residual) formaldehyde, which is generally known to add unpredictability and problems to separation schemes. Although the aldol condensation reaction of acetic acid and formaldehyde is known, there has been little if any disclosure relating to the pre-reaction treatment of the reactants to improve reaction conditions.

Similarly, there has been little if any disclosure relating to separation schemes that may be employed to effectively purify the unique crude product that is produced. Other conventional reactions, e.g., propylene oxidation or ketene/formaldehyde, do not yield crude products that comprises higher amounts of formaldehyde. The primary reactions and the side reactions in propylene oxidation do not create formaldehyde. In the reaction of ketene and formaldehyde, a two-step reaction is employed and the formaldehyde is confined to the first stage. Also, the ketene is highly reactive and converts substantially all of the reactant formaldehyde. As a result of these features, very little, if any, formaldehyde remains in the crude product exiting the reaction zone. Because no formaldehyde is present in crude products formed by these conventional reactions, the separation schemes associated therewith have not addressed the problems and unpredictability that accompany crude products that have higher formaldehyde content.

Crude alkylenating agent compositions are commercially available and are discussed below. These crude alkylenating compositions comprise the alkylenating agent and one or more impurities, e.g., water. One example of a crude alkylenating agent is formalin, which comprises formaldehyde (an exemplary alkylenating agent) as well as water and methanol. As one example, formalin may comprise between 37 wt. % to 55 wt. % formaldehyde, 44 wt. % to 60 wt. % water, and a small amount of methanol. In some embodiments, at least a portion of the water in the formalin is carried through the reaction to the crude acrylate product. In addition, water is formed as a by-product during the aldol condensation reaction. Thus, the resulting crude acrylate product contains a significant portion of water, at least a portion of which must be removed therefrom to obtain an acceptable purified acrylic acid product. One method to remove water is to do so after the crude acrylate product exits the reactor, e.g. downstream of the reactor. This method, however, often requires significant energy resources as the water may be carried through various units in the purification scheme. In addition to the separation problems, the water in the formalin are also believed to negatively affect the stability and/or lifetime of the aldol condensation catalyst.

The inventors have discovered that the aldol condensation reaction conditions are greatly improved by removing water from the crude alkylenating agent feed material, e.g., the formaldehyde source, e.g., formalin, prior to the aldol condensation reaction. Surprisingly and unexpectedly, by removing water prior to the reaction, significantly less energy is required to achieve a suitable purified acrylate product, as compared to removing water downstream of the reactor. As such, the separation and/or overall production efficiencies are beneficially improved, while maintaining the quality of the purified acrylate product. In addition, the removal of water has now been found to improve the stability and lifetime of the catalyst. Therefore, the removal of water in accordance with the present invention surprisingly and unexpectedly improves the catalytic activity of the formation of acrylic acid. As a result, the crude acrylate product comprises a higher yield of acrylate product as compared to a similar reaction in which water is not removed from the alkylenating agent feed material.

In one embodiment, the present invention is to a process for producing acrylic acid, methacrylic acid, and/or the salts and esters thereof. As used herein, acrylic acid, methacrylic acid, and/or the salts and esters thereof, collectively or individually, may be referred to as "acrylate product" or "acrylate products." The use of the terms acrylic acid, methacrylic acid, or the salts and esters thereof, individually, does not exclude the other acrylate products, and the use of the term acrylate product does not require the presence of acrylic acid, methacrylic acid, and the salts and esters thereof.

The inventive process, in one embodiment, includes the step of dehydrating a crude alkylenating agent stream that initially comprises alkylenating agent and water to form a dehydrated alkylenating agent stream and a water stream. Preferably, the dehydrating step may remove at least 15% of the water from the crude alkylenating agent stream, e.g., at least 30%, at least 50%, or at least 80%. In terms of ranges, the dehydrating step may remove from 5% to 90% of the water from the crude alkylenating agent stream, e.g., from 15% to 85%, from 30% to 80%, or from 40% to 70%. In one embodiment, the dehydrated alkylenating stream may comprise less than 50 wt. % water, e.g., less than 35 wt. %, less than 25 wt. %, or less than 15 wt. %. In terms of ranges, the dehydrated alkylenating stream may comprise from 15 wt. % to 75 wt. % water, from 30 wt. % to 65 wt. %, or from 40 wt. % to 50 wt. %. The water stream that is removed from the crude alkylenating stream comprises primarily water, e.g., at least 60 wt. % or at least 80 wt. %.

In some embodiments, the dehydrating step may remove a small amount of alkylenating agent from the crude alkylenating agent stream. Preferably, the dehydrating step removes less than 50% of the alkylenating agent from the crude alkylenating agent stream, i.e., less than 40%, less than 20%, or less than 15%. In terms of ranges, the dehydrating step removes from 5% to 50% of the alkylenating agent from the crude alkylenating agent stream, i.e., from 10% to 40%, or from 15% to 30%.

In some embodiments, the crude alkylenating agent stream contains methanol. In some embodiments, the dehydrating step may remove methanol from the crude alkylenating agent stream thereby yielding a dehydrated alkylenating agent stream that is substantially free of methanol, e.g., that comprises less than 1 wt. %, less than 2 wt. %, or less than 5 wt. %. Preferably, the dehydrating step removes at least 60% of the methanol from the crude alkylenating stream, e.g., at least 75%, at least 90%, or at least 99%. In terms of ranges, the dehydrating step may remove from 50% to 99% of the methanol from the crude alkylenating agent stream, e.g., from 60% to 90% or from 70% to 80%.

In one embodiment, the crude alkylenating agent is dehydrated using a dehydration unit. The dehydration unit may vary widely and may employ any suitable dehydration device or combination of dehydration devices. In one embodiment, the dehydration unit may comprise one or more evaporators. In one embodiment, preferably, the dehydration unit may comprise a series of evaporators. In one embodiment, the dehydration unit may be a multi-stage evaporator. In another embodiment, the crude alkylenating agent is dehydrated using one or more distillation column.

The inventive process, in one embodiment, includes the step of providing a crude acrylate product stream comprising the acrylate products. In a preferred embodiment, the crude product stream is the reaction product of acetic acid and at least a portion of the dehydrated alkylenating agent stream. The crude product stream of the present invention, unlike most conventional acrylic acid-containing crude products, further comprises a significant portion of at least one alkylenating agent. Preferably, the at least one alkylenating agent is formaldehyde. For example, the crude product stream may comprise at least 0.5 wt. % alkylenating agent(s), e.g., at least 1 wt. %, at least 5 wt. %, at least 7 wt. %, at least 10 wt. %, or at least 25 wt. %. In terms of ranges, the crude product stream may comprise from 0.5 wt. % to 50 wt. % alkylenating agent(s), e.g., from 1 wt. % to 45 wt. %, from 1 wt. % to 25 wt. %, from 1 wt. % to 10 wt. %, or from 5 wt. % to 10 wt. %. In terms of upper limits, the crude product stream may comprise at most 50 wt. % alkylenating agent(s), e.g., at most 45 wt. %, at most 25 wt. %, or at most 10 wt. %.

In one embodiment, the crude product stream of the present invention further comprises water. For example, the crude product stream may comprise less than 50 wt. % water, e.g., less than 40 wt. %, less than 30 wt. %, or less than 25 wt. %. In terms of ranges, the crude product stream may comprise from 1 wt. % to 50 wt. % water, e.g., from 5 wt. % to 40 wt. %, from 10 wt. % to 30 wt. %, or from 15 wt. % to 25 wt. %. In terms of upper limits, the crude product stream may comprise at least 1 wt. % water, e.g., at least 5 wt. %, at least 10 wt. %, or at least 15 wt. %. As noted above, the crude acrylate product stream of the present invention comprises less water than conventional crude product streams formed using an alkylenating agent feed material that has not been dehydrated. As a result, the separation scheme, advantageously, does not have to remove as much water to achieve the desired purified acrylate product.

In one embodiment, the crude product stream of the present invention comprises very little, if any, of the impurities found in most conventional acrylic acid crude product streams. For example, the crude product stream of the present invention may comprise less than 1000 wppm of such impurities (either as individual components or collectively), e.g., less than 500 wppm, less than 100 wppm, less than 50 wppm, or less than 10 wppm. Exemplary impurities include acetylene, ketene, beta-propiolactone, higher alcohols, e.g., $C_{2+}$, $C_{3+}$, or $C_{4+}$, and combinations thereof. Importantly, the crude product stream of the present invention comprises very little, if any, furfural and/or acrolein. In one embodiment, the crude product stream comprises substantially no furfural and/or acrolein, e.g., no furfural and/or acrolein. In one embodiment, the crude product stream comprises less than less than 500 wppm acrolein, e.g., less than 100 wppm, less than 50 wppm, or less than 10 wppm. In one embodiment, the crude product stream comprises less than less than 500 wppm furfural, e.g., less than 100 wppm, less than 50 wppm, or less than 10 wppm. Furfural and acrolein are known to act as detrimental chain terminators in acrylic acid polymerization reactions. Also, furfural and/or acrolein are known to have adverse effects on the color of purified product and/or to subsequent polymerized products.

In addition to the acrylic acid and the alkylenating agent, the crude product stream may further comprise acetic acid, water, propionic acid, and light ends such as oxygen, nitrogen, carbon monoxide, carbon dioxide, methanol, methyl acetate, methyl acrylate, acetaldehyde, hydrogen, and acetone. Exemplary compositional data for the crude product stream are shown in Table 1. Components other than those listed in Table 1 may also be present in the crude product stream.

TABLE 1

| CRUDE ACRYLATE PRODUCT STREAM COMPOSITIONS | | | | |
|---|---|---|---|---|
| Component | Conc. (wt. %) | Conc. (wt. %) | Conc. (wt. %) | Conc. (wt. %) |
| Acrylic Acid | 1 to 75 | 1 to 50 | 5 to 50 | 10 to 40 |
| Alkylenating Agent(s) | 0.5 to 50 | 1 to 45 | 1 to 25 | 1 to 10 |
| Acetic Acid | 1 to 90 | 1 to 70 | 5 to 50 | 10 to 50 |
| Water | 1 to 50 | 5 to 40 | 10 to 30 | 15 to 25 |
| Propionic Acid | 0.01 to 10 | 0.1 to 10 | 0.1 to 5 | 0.1 to 1 |
| Oxygen | 0.01 to 10 | 0.1 to 10 | 0.1 to 5 | 0.1 to 1 |
| Nitrogen | 0.1 to 20 | 0.1 to 10 | 0.5 to 5 | 0.5 to 4 |
| Carbon Monoxide | 0.01 to 10 | 0.1 to 10 | 0.1 to 5 | 0.5 to 3 |
| Carbon Dioxide | 0.01 to 10 | 0.1 to 10 | 0.1 to 5 | 0.5 to 3 |
| Other Light Ends | 0.01 to 10 | 0.1 to 10 | 0.1 to 5 | 0.5 to 3 |

The unique crude product stream of the present invention may be separated in a separation zone to form a final product, e.g., a (purified) final acrylic acid product. In one embodiment, the inventive process comprises the step of separating at least a portion of the crude product stream to form an alkylenating agent stream and an intermediate product stream. This separating step may be referred to as an "alkylenating agent split." In one embodiment, the alkylenating agent stream comprises significant amounts of alkylenating agent(s). For example, the alkylenating agent stream may comprise at least 1 wt. % alkylenating agent(s), e.g., at least 5 wt. %, at least 10 wt. %, at least 15 wt. %, or at least 25 wt. %. In terms of ranges, the alkylenating stream may comprise from 1 wt. % to 75 wt. % alkylenating agent(s), e.g., from 3 wt. % to 50 wt. %, from 3 wt. % to 25 wt. %, or from 10 wt. % to 20 wt. %. In terms of upper limits, the alkylenating stream may comprise less than 75 wt. % alkylenating agent(s), e.g. less than 50 wt. % or less than 40 wt. %. In preferred embodiments, the alkylenating agent is formaldehyde.

As noted above, the presence of alkylenating agent in the crude product stream adds unpredictability and problems to separation schemes. Without being bound by theory, it is believed that formaldehyde reacts in many side reactions with water to form by-products. The following side reactions are exemplary.

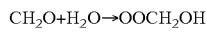

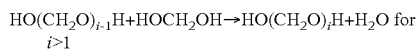

Without being bound by theory, it is believed that, in some embodiments, as a result of these reactions, the alkylenating agent, e.g., formaldehyde, acts as a "light" component at higher temperatures and as a "heavy" component at lower temperatures. The reaction(s) are exothermic. Accordingly, the equilibrium constant increases as temperature decreases and decreases as temperature increases. At lower temperatures, the larger equilibrium constant favors methylene glycol and oligomer production and formaldehyde becomes limited, and, as such, behaves as a heavy component. At higher temperatures, the smaller equilibrium constant favors formaldehyde production and methylene glycol becomes limited. As such, formaldehyde behaves as a light component. In view of these difficulties, as well as others, the separation of streams that comprise water and formaldehyde cannot be expected to behave as a typical two-component system. These features contribute to the unpredictability and difficulty of the separation of the unique crude product stream of the present invention.

The present invention, surprisingly and unexpectedly, achieves effective separation of alkylenating agent(s) from the inventive crude product stream to yield a purified product comprising acrylate product and very low amounts of other impurities.

In one embodiment, the alkylenating split is performed such that a lower amount of acetic acid is present in the resulting alkylenating stream. Preferably, the alkylenating agent stream comprises little or no acetic acid. As an example, the alkylenating agent stream, in some embodiments, comprises less than 50 wt. % acetic acid, e.g., less than 45 wt. %, less than 25 wt. %, less than 10 wt. %, less than 5 wt. %, less than 3 wt. %, or less than 1 wt. %. Surprisingly and unexpectedly, the present invention provides for the lower amounts of acetic acid in the alkylenating agent stream, which, beneficially reduces or eliminates the need for further treatment of the alkylenating agent stream to remove acetic acid. In some embodiments, the alkylenating agent stream may be treated to remove water therefrom, e.g., to purge water.

In some embodiments, the alkylenating agent split is performed in at least one column, e.g., at least two columns or at least three columns. Preferably, the alkylenating agent is performed in a two column system. In other embodiments, the alkylenating agent split is performed via contact with an extraction agent. In other embodiments, the alkylenating agent split is performed via precipitation methods, e.g., crystallization, and/or azeotropic distillation. Of course, other suitable separation methods may be employed either alone or in combination with the methods mentioned herein.

The intermediate product stream comprises acrylate products. In one embodiment, the intermediate product stream comprises a significant portion of acrylate products, e.g., acrylic acid. For example, the intermediate product stream may comprise at least 5 wt. % acrylate products, e.g., at least 25 wt. %, at least 40 wt. %, at least 50 wt. %, or at least 60 wt. %. In terms of ranges, the intermediate product stream may comprise from 5 wt. % to 99 wt. % acrylate products, e.g. from 10 wt. % to 90 wt. %, from 25 wt. % to 75 wt. %, or from 35 wt. % to 65 wt. %. The intermediate product stream, in one embodiment, comprises little if any alkylenating agent. For example, the intermediate product stream may comprise less than 1 wt. % alkylenating agent, e.g., less than 0.1 wt. %, less than 0.05 wt. %, or less than 0.01 wt. %. In addition to the acrylate products, the intermediate product stream optionally comprises acetic acid, water, propionic acid and other components.

In some cases, the intermediate acrylate product stream comprises higher amounts of alkylenating agent. For example, in one embodiment, the intermediate acrylate product stream comprises from 1 wt. % to 50 wt. % alkylenating agent, e.g., from 1 wt. % to 10 wt. % or from 5 wt. % to 50 wt. %. In terms of limits, the intermediate acrylate product stream may comprise at least 1 wt. % alkylenating agent, e.g., at least 5 wt. % or at least 10 wt. %.

In one embodiment, the crude product stream is optionally treated, e.g. separated, prior to the separation of alkylenating agent therefrom. In such cases, the treatment(s) occur before the alkylenating agent split is performed. In other embodiments, at least a portion of the intermediate acrylate product stream may be further treated after the alkylenating agent split. As one example, the crude product stream may be treated to remove light ends therefrom. This treatment may occur either before or after the alkylenating agent split, preferably before the alkylenating agent split. In some of these cases, the further treatment of the intermediate acrylate product stream may result in derivative streams that may be considered to be additional purified acrylate product streams. In other embodiments, the further treatment of the intermediate acrylate product stream results in at least one finished acrylate product stream.

In one embodiment, the inventive process operates at a high process efficiency. For example, the process efficiency may be at least 10%, e.g., at least 20% or at least 35%. In one embodiment, the process efficiency is calculated based on the flows of reactants into the reaction zone. The process efficiency may be calculated by the following formula.

$$\text{Process Efficiency} = 2N_{HAcA}/[N_{HoAc}+N_{HCHO}+N_{H2O}]$$

where:

$N_{HAcA}$ is the molar production rate of acrylate products; and $N_{HOAc}$, $N_{HCHO}$, and $N_{H2O}$ are the molar feed rates of acetic acid, formaldehyde, and water.

Production of Acrylate Products

Any suitable reaction and/or separation scheme may be employed to form the crude product stream as long as the reaction provides the crude product stream components that are discussed above. For example, in some embodiments, the acrylate product stream is formed by contacting an alkanoic acid, e.g., acetic acid, or an ester thereof with an alkylenating agent, e.g., a methylenating agent, for example formaldehyde, under conditions effective to form the crude acrylate product stream. Preferably, the contacting is performed over a suitable catalyst. The crude product stream may be the reaction product of the alkanoic acid-alkylenating agent reaction. In a preferred embodiment, the crude product stream is the reaction product of the aldol condensation reaction of acetic acid and formaldehyde, which is conducted over a catalyst comprising vanadium and titanium. In one embodiment, the crude product stream is the product of a reaction where methanol and acetic acid are combined to generate formaldehyde in situ. The aldol condensation then follows. In one embodiment, a methanol-formaldehyde solution is reacted with acetic acid to form the crude product stream.

The alkanoic acid, or an ester of the alkanoic acid, may be of the formula R'—CH$_2$—COOR, where R and R' are each, independently, hydrogen or a saturated or unsaturated alkyl or aryl group. As an example, R and R' may be a lower alkyl group containing for example 1-4 carbon atoms. In one embodiment, an alkanoic acid anhydride may be used as the source of the alkanoic acid. In one embodiment, the reaction is conducted in the presence of an alcohol, preferably the alcohol that corresponds to the desired ester, e.g., methanol. In addition to reactions used in the production of acrylic acid, the inventive catalyst, in other embodiments, may be employed to catalyze other reactions.

The alkanoic acid, e.g., acetic acid, may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352, which is hereby incorporated by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syngas is diverted from the methanol synthesis loop and supplied to a separator unit to recover carbon monoxide and hydrogen, which are then used to produce acetic acid.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, all of which are hereby incorporated by reference.

U.S. Pat. No. RE 35,377, which is hereby incorporated by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. U.S. Pat. No. 5,821,111, which discloses a process for converting waste biomass through gasification into syngas, as well as U.S. Pat. No. 6,685,754 are hereby incorporated by reference.

In one optional embodiment, the acetic acid that is utilized in the condensation reaction comprises acetic acid and may also comprise other carboxylic acids, e.g., propionic acid, esters, and anhydrides, as well as acetaldehyde and acetone. In one embodiment, the acetic acid fed to the condensation reaction comprises propionic acid. For example, the acetic acid fed to the reaction may comprise from 0.001 wt. % to 15 wt. % propionic acid, e.g., from 0.001 wt. % to 0.11 wt. %, from 0.125 wt. % to 12.5 wt. %, from 1.25 wt. % to 11.25 wt. %, or from 3.75 wt. % to 8.75 wt. %. Thus, the acetic acid feed stream may be a cruder acetic acid feed stream, e.g., a less-refined acetic acid feed stream.

As used herein, "alkylenating agent" means an aldehyde or precursor to an aldehyde suitable for reacting with the alkanoic acid, e.g., acetic acid, to form an unsaturated acid, e.g., acrylic acid, or an alkyl acrylate. In preferred embodiments, the alkylenating agent comprises a methylenating agent such as formaldehyde, which preferably is capable of adding a methylene group (=CH$_2$) to the organic acid. Other alkylenating agents may include, for example, acetaldehyde, propanal, butanal, aryl aldehydes, benzyl aldehydes, alcohols, and combinations thereof. This listing is not exclusive and is not meant to limit the scope of the invention. In one embodiment, an alcohol may serve as a source of the alkylenating agent. For example, the alcohol may be reacted in situ to form the alkylenating agent, e.g., the aldehyde.

The alkylenating agent, e.g., formaldehyde, may be derived from any suitable source. Exemplary sources may include, for example, aqueous formaldehyde solutions, anhydrous formaldehyde derived from a formaldehyde drying procedure, trioxane, diether of methylene glycol, and paraformaldehyde. In a preferred embodiment, the formaldehyde is produced via a a methanol oxidation process, which reacts methanol and oxygen to yield the formaldehyde.

In other embodiments, the alkylenating agent is a compound that is a source of formaldehyde. Where forms of formaldehyde that are not as freely or weakly complexed are used, the formaldehyde will form in situ in the condensation reactor or in a separate reactor prior to the condensation reactor. Thus for example, trioxane may be decomposed over an inert material or in an empty tube at temperatures over 350° C. or over an acid catalyst at over 100° C. to form the formaldehyde.

In one embodiment, the alkylenating agent corresponds to Formula I.

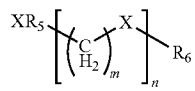

In this formula, R$_5$ and R$_6$ may be independently selected from C$_1$-C$_{12}$ hydrocarbons, preferably, C$_1$-C$_{12}$ alkyl, alkenyl or aryl, or hydrogen. Preferably, R$_5$ and R$_6$ are independently C$_1$-C$_6$ alkyl or hydrogen, with methyl and/or hydrogen being most preferred. X may be either oxygen or sulfur, preferably oxygen; and n is an integer from 1 to 10, preferably 1 to 3. In some embodiments, m is 1 or 2, preferably 1.

In one embodiment, the compound of formula I may be the product of an equilibrium reaction between formaldehyde and methanol in the presence of water. In such a case, the compound of formula I may be a suitable formaldehyde source. In one embodiment, the formaldehyde source includes any equilibrium composition. Examples of formaldehyde sources include but are not restricted to methylal (1,1 dimethoxymethane); polyoxymethylenes —(CH$_2$—O)$_i$— wherein i is from 1 to 100; formalin; and other equilibrium compositions such as a mixture of formaldehyde, methanol, and methyl propionate. In one embodiment, the source of formaldehyde is selected from the group consisting of 1,1 dimethoxymethane; higher formals of formaldehyde and methanol; and CH$_3$—O—(CH$_2$—O)$_i$—CH$_3$ where i is 2.

The alkylenating agent may be used with or without an organic or inorganic solvent.

As discussed above, in some embodiments, the alkylenating agent that is reacted with the alkanoic acid may be provided to the process in the form of a crude alkylenating agent stream. The crude alkylenating agent stream comprises alkylenating agent, e.g., formaldehyde, and at least one other impurity, e.g., water and/or methanol. Preferably, the crude alkylenating agent stream comprises formalin. The term "formalin," refers to a mixture of formaldehyde, methanol, and water. In one embodiment, formalin comprises from 37 wt. % to 55 wt. % formaldehyde, from 44 wt. % to 60 wt. % water, and from 0.01 wt. % to 25 wt. % methanol. In cases where a mixture of formaldehyde, methanol, and methyl propionate is used, the mixture comprises less than 10 wt. % water, e.g., less than 5 wt. % or less than 1 wt. %. In accordance with the present invention, the crude alkylenating agent may be dehydrated to reduce impurity content in the crude alkylenating agent stream, e.g., to remove water from the crude alkylenating agent stream.

In some embodiments, the condensation reaction may achieve favorable conversion of acetic acid and favorable selectivity and productivity to acrylates. For purposes of the present invention, the term "conversion" refers to the amount of acetic acid in the feed that is converted to a compound other than acetic acid. Conversion is expressed as a percentage based on acetic acid in the feed. The conversion of acetic acid may be at least 10%, e.g., at least 20%, at least 40%, or at least 50%.

Selectivity, as it refers to the formation of acrylate product, is expressed as the ratio of the amount of carbon in the desired product(s) and the amount of carbon in the total products. This ratio may be multiplied by 100 to arrive at the selectivity. Preferably, the catalyst selectivity to acrylate products, e.g., acrylic acid and methyl acrylate, is at least 40 mol %, e.g., at least 50 mol %, at least 60 mol %, or at least 70 mol %. In some embodiments, the selectivity to acrylic acid is at least 30 mol %, e.g., at least 40 mol %, or at least 50 mol %; and/or the selectivity to methyl acrylate is at least 10 mol %, e.g., at least 15 mol %, or at least 20 mol %.

The terms "productivity" or "space time yield" as used herein, refers to the grams of a specified product, e.g., acrylate products, formed per hour during the condensation based on the liters of catalyst used. A productivity of at least 20 grams of acrylate product per liter catalyst per hour, e.g., at least 40 grams of acrylates per liter catalyst per hour or at least 100 grams of acrylates per liter catalyst per hour, is preferred. In terms of ranges, the productivity preferably is from 20 to 700 grams of acrylates per liter catalyst per hour, e.g., from 20 to 300 grams of acrylates per kilogram catalyst per hour or from 40 to 200 grams of acrylates per kilogram catalyst per hour.

In one embodiment, the inventive process yields at least 1,800 kg/hr of finished acrylic acid, e.g., at least 3,500 kg/hr, at least 18,000 kg/hr, or at least 37,000 kg/hr.

Preferred embodiments of the inventive process demonstrate a low selectivity to undesirable products, such as carbon monoxide and carbon dioxide. The selectivity to these undesirable products preferably is less than 29%, e.g., less than 25% or less than 15%. More preferably, these undesirable products are not detectable. Formation of alkanes, e.g., ethane, may be low, and ideally less than 2%, less than 1%, or less than 0.5% of the acetic acid passed over the catalyst is converted to alkanes, which have little value other than as fuel.

The alkanoic acid or ester thereof and alkylenating agent may be fed independently or after prior mixing to a reactor containing the catalyst. The reactor may be any suitable reactor or combination of reactors. Preferably, the reactor comprises a fixed bed reactor or a series of fixed bed reactors. In one embodiment, the reactor is a packed bed reactor or a series of packed bed reactors. In one embodiment, the reactor is a fixed bed reactor. Of course, other reactors such as a continuous stirred tank reactor or a fluidized bed reactor, may be employed.

In some embodiments, the alkanoic acid, e.g., acetic acid, and the alkylenating agent, e.g., formaldehyde, are fed to the reactor at a molar ratio of at least 0.10:1, e.g., at least 0.75:1 or at least 1:1. In terms of ranges the molar ratio of alkanoic acid to alkylenating agent may range from 0.10:1 to 10:1 or from 0.75:1 to 5:1. In some embodiments, the reaction of the alkanoic acid and the alkylenating agent is conducted with a stoichiometric excess of alkanoic acid. In these instances, acrylate selectivity may be improved. As an example the acrylate selectivity may be at least 10% higher than a selectivity achieved when the reaction is conducted with an excess of alkylenating agent, e.g., at least 20% higher or at least 30% higher. In other embodiments, the reaction of the alkanoic acid and the alkylenating agent is conducted with a stoichiometric excess of alkylenating agent.

The condensation reaction may be conducted at a temperature of at least 250° C., e.g., at least 300° C., or at least 350° C. In terms of ranges, the reaction temperature may range from 200° C. to 500° C., e.g., from 250° C. to 400° C., or from 250° C. to 350° C. Residence time in the reactor may range from 1 second to 200 seconds, e.g., from 1 second to 100 seconds. Reaction pressure is not particularly limited, and the reaction is typically performed near atmospheric pressure. In one embodiment, the reaction may be conducted at a pressure ranging from 0 kPa to 4100 kPa, e.g., from 3 kPa to 345 kPa, or from 6 kPa to 103 kPa. The acetic acid conversion, in some embodiments, may vary depending upon the reaction temperature.

In one embodiment, the reaction is conducted at a gas hourly space velocity ("GHSV") greater than 600 $hr^{-1}$, e.g., greater than 1000 $hr^{-1}$ or greater than 2000 $hr^{-1}$. In one embodiment, the GHSV ranges from 600 $hr^{-1}$ to 10000 $hr^{-1}$, e.g., from 1000 $hr^{-1}$ to 8000 $hr^{-1}$ or from 1500 $hr^{-1}$ to 7500 $hr^{-1}$. As one particular example, when GHSV is at least 2000 $hr^{-1}$, the acrylate product STY may be at least 150 g/hr/liter.

Water may be present in the reactor in amounts up to 60 wt. %, by weight of the reaction mixture, e.g., up to 50 wt. % or up to 40 wt. %. At least a portion of the water, however, is preferably removed prior to the condensation reaction for the reasons discussed above.

In one embodiment, an inert or reactive gas is supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors. The addition of these additional components may improve reaction efficiencies.

In one embodiment, the unreacted components such as the alkanoic acid and formaldehyde as well as the inert or reactive gases that remain are recycled to the reactor after sufficient separation from the desired product.

When the desired product is an unsaturated ester made by reacting an ester of an alkanoic acid ester with formaldehyde, the alcohol corresponding to the ester may also be fed to the reactor either with or separately to the other components. For example, when methyl acrylate is desired, methanol may be fed to the reactor. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity. In one embodiment, the alcohol may be added downstream of the reactor.

Catalyst Composition

The catalyst may be any suitable catalyst composition. As one example, condensation catalyst consisting of mixed oxides of vanadium and phosphorus have been investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987). Other examples include binary vanadium-titanium phosphates, vanadium-silicaphosphates, and alkali metal-promoted silicas, e.g., cesium- or potassium-promoted silicas.

In a preferred embodiment, the inventive process employs a catalyst composition comprising vanadium, titanium, and optionally at least one oxide additive. The oxide additive(s), if present, are preferably present in the active phase of the catalyst. In one embodiment, the oxide additive(s) are selected from the group consisting of silica, alumina, zirconia, and mixtures thereof or any other metal oxide other than metal oxides of titanium or vanadium. Preferably, the molar ratio of oxide additive to titanium in the active phase of the catalyst composition is greater than 0.05:1, e.g., greater than 0.1:1, greater than 0.5:1, or greater than 1:1. In terms of ranges, the molar ratio of oxide additive to titanium in the inventive catalyst may range from 0.05:1 to 20:1, e.g., from 0.1:1 to 10:1, or from 1:1 to 10:1. In these embodiments, the catalyst comprises titanium, vanadium, and one or more oxide additives and have relatively high molar ratios of oxide additive to titanium.

In other embodiments, the catalyst may further comprise other compounds or elements (metals and/or non-metals). For example, the catalyst may further comprise phosphorus and/or oxygen. In these cases, the catalyst may comprise from 15 wt. % to 45 wt. % phosphorus, e.g., from 20 wt. % to 35 wt. % or from 23 wt. % to 27 wt. %; and/or from 30 wt. % to 75 wt. % oxygen, e.g., from 35 wt. % to 65 wt. % or from 48 wt. % to 51 wt. %.

In some embodiments, the catalyst further comprises additional metals and/or oxide additives. These additional metals and/or oxide additives may function as promoters. If present, the additional metals and/or oxide additives may be selected from the group consisting of copper, molybdenum, tungsten, nickel, niobium, and combinations thereof. Other exemplary promoters that may be included in the catalyst of the invention include lithium, sodium, magnesium, aluminum, chromium, manganese, iron, cobalt, calcium, yttrium, ruthenium, silver, tin, barium, lanthanum, the rare earth metals, hafnium, tantalum, rhenium, thorium, bismuth, antimony, germanium, zirconium, uranium, cesium, zinc, and silicon and mixtures thereof. Other modifiers include boron, gallium, arsenic, sulfur, halides, Lewis acids such as $BF_3$, $ZnBr_2$, and $SnCl_4$. Exemplary processes for incorporating promoters into catalyst are described in U.S. Pat. No. 5,364,824, the entirety of which is incorporated herein by reference.

If the catalyst comprises additional metal(s) and/or metal oxides(s), the catalyst optionally may comprise additional metals and/or metal oxides in an amount from 0.001 wt. % to 30 wt. %, e.g., from 0.01 wt. % to 5 wt. % or from 0.1 wt. % to 5 wt. %. If present, the promoters may enable the catalyst to have a weight/weight space time yield of at least 25 grams of acrylic acid/gram catalyst-h, e.g., least 50 grams of acrylic acid/gram catalyst-h, or at least 100 grams of acrylic acid/gram catalyst-h.

In some embodiments, the catalyst is unsupported. In these cases, the catalyst may comprise a homogeneous mixture or a heterogeneous mixture as described above. In one embodiment, the homogeneous mixture is the product of an intimate mixture of vanadium and titanium oxides, hydroxides, and phosphates resulting from preparative methods such as controlled hydrolysis of metal alkoxides or metal complexes. In other embodiments, the heterogeneous mixture is the product of a physical mixture of the vanadium and titanium phosphates. These mixtures may include formulations prepared from phosphorylating a physical mixture of preformed hydrous metal oxides. In other cases, the mixture(s) may include a mixture of preformed vanadium pyrophosphate and titanium pyrophosphate powders.

In another embodiment, the catalyst is a supported catalyst comprising a catalyst support in addition to the vanadium, titanium, oxide additive, and optionally phosphorous and oxygen, in the amounts indicated above (wherein the molar ranges indicated are without regard to the moles of catalyst support, including any vanadium, titanium, oxide additive, phosphorous or oxygen contained in the catalyst support). The total weight of the support (or modified support), based on the total weight of the catalyst, preferably is from 75 wt. % to 99.9 wt. %, e.g., from 78 wt. % to 97 wt. %, or from 80 wt. % to 95 wt. %. The support may vary widely. In one embodiment, the support material is selected from the group consisting of silica, alumina, zirconia, titania, aluminosilicates, zeolitic materials, mixed metal oxides (including but not limited to binary oxides such as $SiO_2$—$Al_2O_3$, $SiO_2$—$TiO_2$, $SiO_2$—$ZnO$, $SiO_2$—$MgO$, $SiO_2$—$ZrO_2$, $Al_2O_3$—$MgO$, $Al_2O_3$—$TiO_2$, $Al_2O_3$—$ZnO$, $TiO_2$—$MgO$, $TiO_2$—$ZrO_2$, $TiO_2$—$ZnO$, $TiO_2$—$SnO_2$) and mixtures thereof, with silica being one preferred support. In embodiments where the catalyst comprises a titania support, the titania support may comprise a major or minor amount of rutile and/or anatase titanium dioxide. Other suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, silicon carbide, sheet silicates or clay minerals such as montmorillonite, beidellite, saponite, pillared clays, other microporous and mesoporous materials, and mixtures thereof. Other supports may include, but are not limited to, iron oxide, magnesia, steatite, magnesium oxide, carbon, graphite, high surface area graphitized carbon, activated carbons, and mixtures thereof. These listings of supports are merely exemplary and are not meant to limit the scope of the present invention.

In some embodiments, a zeolitic support is employed. For example, the zeolitic support may be selected from the group consisting of montmorillonite, $NH_4$ ferrierite, H-mordenite-PVOx, vermiculite-1, H-ZSMS, NaY, H-SDUSY, Y zeolite with high SAR, activated bentonite, H-USY, MONT-2, HY, mordenite SAR 20, SAPO-34, Aluminosilicate (X), VUSY, Aluminosilicate (CaX), Re—Y, and mixtures thereof. H-SDUSY, VUSY, and H-USY are modified Y zeolites belonging to the faujasite family. In one embodiment, the support is a zeolite that does not contain any metal oxide modifier(s). In some embodiments, the catalyst composition comprises a zeolitic support and the active phase comprises a metal selected from the group consisting of vanadium, aluminum, nickel, molybdenum, cobalt, iron, tungsten, zinc, copper, titanium cesium bismuth, sodium, calcium, chromium, cadmium, zirconium, and mixtures thereof. In some of these embodiments, the active phase may also comprise hydrogen, oxygen, and/or phosphorus.

In other embodiments, in addition to the active phase and a support, the inventive catalyst may further comprise a support modifier. A modified support, in one embodiment, relates to a support that includes a support material and a support modifier, which, for example, may adjust the chemical or physical properties of the support material such as the acidity or basicity of the support material. In embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst composition.

In one embodiment, the support modifier is an acidic support modifier. In some embodiments, the catalyst support is modified with an acidic support modifier. The support modifier similarly may be an acidic modifier that has a low volatility or little volatility. The acidic modifiers may be selected from the group consisting of oxides of Group IVB metals, oxides of Group VB metals, oxides of Group VIB metals, iron oxides, aluminum oxides, and mixtures thereof. In one embodiment, the acidic modifier may be selected from the group consisting of $WO_3$, $MoO_3$, $Fe_2O_3$, $Cr_2O_3$, $V_2O_5$, $MnO_2$, $CuO$, $Co_2O_3$, $Bi_2O_3$, $TiO_2$, $ZrO_2$, $Nb_2O_5$, $Ta_2O_5$, $Al_2O_3$, $B_2O_3$, $P_2O_5$, and $Sb_2O_3$.

In another embodiment, the support modifier is a basic support modifier. The presence of chemical species such as alkali and alkaline earth metals, are normally considered basic and may conventionally be considered detrimental to catalyst performance. The presence of these species, however, surprisingly and unexpectedly, may be beneficial to the catalyst performance. In some embodiments, these species may act as catalyst promoters or a necessary part of the acidic catalyst structure such in layered or sheet silicates such as montmorillonite. Without being bound by theory, it is postulated that these cations create a strong dipole with species that create acidity.

Additional modifiers that may be included in the catalyst include, for example, boron, aluminum, magnesium, zirconium, and hafnium.

As will be appreciated by those of ordinary skill in the art, the support materials, if included in the catalyst of the present invention, preferably are selected such that the catalyst system is suitably active, selective and robust under the process conditions employed for the formation of the desired product, e.g., acrylic acid or alkyl acrylate. Also, the active metals and/or pyrophosphates that are included in the catalyst of the invention may be dispersed throughout the support, coated on the outer surface of the support (egg shell) or decorated on the surface of the support. In some embodiments, in the case of macro- and meso-porous materials, the active sites may be anchored or applied to the surfaces of the pores that are distributed throughout the particle and hence are surface sites available to the reactants but are distributed throughout the support particle.

The inventive catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

Dehydration of Crude Alkylenating Stream

As discussed above, the crude alkylenating agent stream is dehydrated to yield a dehydrated alkylenating agent stream. FIG. 1 is a flow diagram depicting the dehydration of the crude alkylenating stream, formation of the crude acrylates product stream and the separation thereof to obtain a final acrylate acid product. Acrylate product system 100 comprises dehydration zone 102, reaction zone 104, and purification zone 106.

The components of dehydration zone 102 may vary widely and may include dehydration units or combinations of dehydration units that are well known in the art. In an embodiment, dehydration zone 102 comprises at least one evaporator. In another embodiment, dehydration zone 102 comprises at least one distillation column. In another embodiment, dehydration zone 102 comprises at least one vacuum evaporator. Generally speaking, dehydration zone may further comprise crude alkylenating stream feed, e.g., formalin feed, 108. In an embodiment, reaction zone 104 comprises reactor 110, alkanoic acid feed, e.g., acetic acid feed, 112, dehydrated alkylenating agent feed, e.g., dehydrated formalin feed 114, and vaporizer 116. Dehydrated alkylenating agent feed 114 is yielded from dehydration zone 102. In an embodiment, purification zone 106 comprises one or more separation units, e.g., distillation columns, to separate crude acrylate product stream 118 to yield purified acrylate product stream 120.

Figure 2:
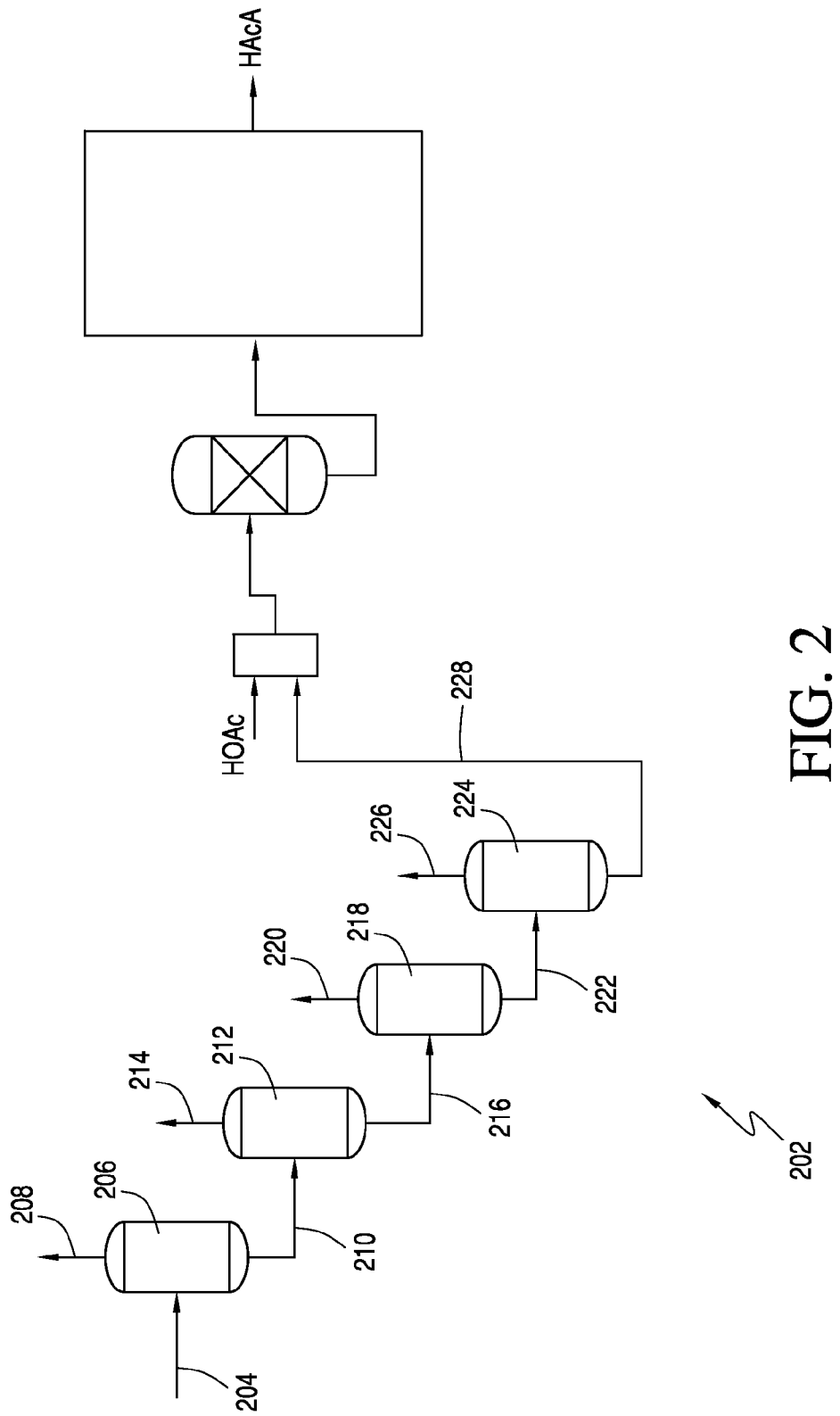
FIG. 2 is a schematic diagram of an acrylic acid reaction/separation system in accordance with one embodiment of the present invention.

FIG. 2. shows an embodiment of a formalin dehydration, reaction, and separation scheme in accordance with the present invention. The dehydration may be accomplished with one or more dehydration units, e.g., two or more or three or more. In FIG. 2, dehydration zone 202 comprises four water removal units, i.e., evaporators 206, 212, 218, and 224. Although FIG. 2 shows four dehydration units, fewer units or more units may be employed. In an embodiment, dehydration zone 202 may comprise a multi-stage evaporator. As shown in FIG. 2, formalin is fed to first evaporator 206 via line 204 to create first water stream 208 and first dehydrated formalin stream 210. The formalin feed may be considered a crude alkylenating agent stream.

The type of evaporator used in the present invention is not particularly limited but may include those of wet wall column system and forced circulation system. In another embodiment, the evaporator may be a shell- and tube type evaporator unit.

In an embodiment, first water stream 208 comprises water, formaldehyde and methanol. For example, first water stream 208 may comprise from 30 wt. % to 90 wt. % water, e.g., from 50 wt. % to 80 wt. % or from 60 wt. % to 70 wt. %. In terms of lower limits, first water stream 208 may comprise at least 30 wt. % water, e.g., at least 50 wt. %, at least 60 wt. % or at least 70 wt. %. In one embodiment, first water stream 208 may comprise from 5 wt. % to 50 wt. % formaldehyde, e.g., from 10 wt. % to 40 wt. %, or from 20 wt. % to 30 wt. %. In terms of ranges, first water stream 208 may comprise at most 40 wt. % formaldehyde, at most 30 wt. % or at most 20 wt. %. In one embodiment, the water stream 208 may comprise less than 10 wt. % methanol, e.g., less than 7 wt. %, less than 5 wt. % or less than 3 wt. %.

In an embodiment, first dehydrated formalin stream 210 comprises less water than formalin feed in line 204. In an embodiment, first dehydrated formalin stream 210 comprises water and formaldehyde. For example, first dehydrated formalin stream 210 may comprise from 30 wt. % to 90 wt. % formaldehyde, e.g., from 50 wt. % to 80 wt. % or from 60 wt. % to 70 wt. %. In terms of lower limits, first dehydrated formalin stream 210 may comprise at least 30 wt. % formaldehyde, e.g., at least 50 wt. % or at least 60 wt. %. In one embodiment, first dehydrated formalin stream 210 may comprise from 10 wt. % to 70 wt. % water, e.g., from 20 wt. % to 60 wt. %, or from 30 wt. % to 40 wt. %. In terms of upper limit, first dehydrated formalin stream 210 may comprise at most 70 wt. % water, e.g., at most 60 wt. %, 50 wt. % or 40 wt. %. In one embodiment, first dehydrated formalin stream 210 is substantially free of methanol, e.g., less than 3 wt. %, less than 1 wt. %, or less than 0.5 wt. %.

In an embodiment, first evaporator 206 removes from 20% to 90% of the water from formalin in line 204, e.g., from 30% to 75%, from 40% to 60%. In an embodiment, first evaporator 206 removes less than 50% of the formaldehyde from formalin in line 204, e.g., removes less than 30%, less than 20%, or less than 15%.

Exemplary compositional ranges for the first water stream and the first dehydrated formalin stream of first evaporator 206 are shown in Table 2. Components other than those listed in Table 2 may also be present in the water stream and the dehydrated formalin stream.

TABLE 2

| FIRST EVAPORATOR | | | |
| --- | --- | --- | --- |
|  | Conc. (wt. %) | Conc. (wt. %) | Conc. (wt. %) |
| First Water Stream | | | |
| Water | 30 to 90 | 50 to 80 | 60 to 75 |
| Formaldehyde | 5 to 50 | 10 to 40 | 20 to 30 |
| Methanol | <10 | <5 | <3 |
| First Dehydrated Stream | | | |
| Formaldehyde | 30 to 90 | 50 to 80 | 60 to 70 |
| Water | 10 to 70 | 20 to 60 | 30 to 40 |
| Methanol | <3 | <1 | <500 ppm |

[Please confirm that these ranges are accurate]

In one embodiment, the temperature of the water stream exiting the evaporator ranges from 20° C. to 100° C., e.g., from 30° C. to 80° C., from 35° C. to 70° C., or from 45° C. to 55° C. In one embodiment, the pressure at which the evaporator is operated may range from 1 kPa to 300 kPa, e.g., from 5 kPa to 100 kPa, or from 10 kPa to 50 kPa.

In an embodiment, depending on the amount of water in the first dehydrated formalin stream, water may be further removed from the first dehydrated formalin stream using additional evaporators. As shown in FIG. 2, first dehydrated formalin stream may be fed to second evaporator 212 via line 210 to create second water stream 214 and second dehydrated formalin stream 216. In one embodiment, the temperature of the first dehydrated stream ranges from 20° C. to 100° C., e.g., from 30° C. to 80° C., from 35° C. to 70° C., or from 45° C. to 55° C.

Preferably, second dehydrated formalin stream 216 contains less water than first dehydrated formalin stream 210. For example, in one embodiment, second dehydrated formalin stream 216 may comprise from 10 wt. % to 70 wt. % water, e.g., from 20 wt. % to 60 wt. %, or from 30 wt. % to 40 wt. %. In terms of upper limits, second dehydrated formalin stream 216 may comprise at most 70 wt. % water, e.g., at most 60 wt. %, at most 50 wt. %, or at most 40 wt. %. In one embodiment, second dehydrated formalin stream 216 may comprise from 40 wt. % to 90 wt. % formaldehyde, e.g., from 50 wt. % to 80 wt. % or from 60 wt. % to 70 wt. %. In terms of lower limits, second formalin stream 216 may comprise at least 40 wt. % formaldehyde, at least 50 wt. %, or at least 60 wt. %. In one embodiment, second dehydrated formalin stream 216 is substantially free of methanol, e.g., less than 3 wt. %, less than 1 wt. %, or less than 0.5 wt. %.

In an embodiment, second water stream 214 may comprise from 30 wt. % to 90 wt. % water, e.g., from 50 wt. % to 80 wt. % or from 60 wt. % to 70 wt. %. In terms of lower limits, second water stream 214 may comprise at least 30 wt. % water, at least 50 wt. %, or at least 60 wt. %. In one embodiment, water stream 214 may comprise from 10 wt. % to 50 wt. % formaldehyde, e.g., from 20 wt. % to 45 wt. %, or from 30 wt. % to 40 wt. %. In terms of upper limits, water stream 214 may comprise at most 45 wt. % formaldehyde, e.g., at most 40 wt. %, or at most 30 wt. %. In one embodiment, the water stream 214 may comprise less than 5 wt. % methanol, e.g., less than 3 wt. %, or less than 1 wt. %.

In an embodiment, second evaporator 212 removes from 20 wt. % to 50 wt. % of the water from first dehydrated formalin stream in line 210, e.g., from 25 wt. % to 45 wt. %, from 30 wt. % to 40 wt. %. In terms of lower limits, second evaporator 212 removes at least 20 wt. % of the water from first dehydrated formalin stream, e.g., at least 25 wt. %, or at least 30 wt. %. In an embodiment, second evaporator 212 removes less than 30 wt. % of the formaldehyde from first dehydrated formalin stream in line 210, e.g., removes less than 20 wt. %, less than 15 wt. %, or less than 10 wt. %.

Exemplary compositional ranges for the second water stream and the second dehydrated formalin stream of second evaporator are shown in Table 3. Components other than those listed in Table 3 may also be present in the water stream and the dehydrated formalin stream.

TABLE 3

| SECOND EVAPORATOR | | | |
| --- | --- | --- | --- |
|  | Conc. (wt. %) | Conc. (wt. %) | Conc. (wt. %) |
| Second Water Stream | | | |
| Water | 30 to 90 | 50 to 80 | 60 to 70 |
| Formaldehyde | 10 to 50 | 20 to 45 | 30 to 40 |
| Methanol | <5 | <3 | <1 |
| Second Dehydrated Stream | | | |
| Formaldehyde | 30 to 90 | 50 to 80 | 60 to 70 |
| Water | 20 to 70 | 20 to 60 | 30 to 40 |
| Methanol | <3 | <1 | <500 ppm |

In one embodiment, the temperature of the second water stream exiting the second evaporator ranges from 20° C. to 100° C., e.g., from 30° C. to 80° C., from 35° C. to 70° C., or from 45° C. to 55° C. In one embodiment, the pressure at which the evaporator is operated may range from 1 kPa to 300 kPa, e.g., from 5 kPa to 100 kPa, or from 10 kPa to 50 kPa.

As stated above, depending on the amount of water in the second dehydrated formalin stream, water may be further removed from the first or second dehydrated formalin stream using additional evaporators. As shown in FIG. 2, a third and a forth evaporators may be used to further lower the water content in the second dehydrated formalin stream 216. In a preferred embodiment, third dehydrated formalin stream in line 222 from third evaporator 218 contains less water than the second dehydrated formalin stream in line 216. Similarly, the fourth formalin stream in line 228 from fourth evaporator 224 contains less water than the third dehydrated formalin stream in line 222.

As shown in FIG. 2, second dehydrated formalin stream in line 216 may be fed to third evaporator 218 to create third water stream 220 and third dehydrated formalin stream 222. If desired, third dehydrated formalin stream 222 may be fed to fourth evaporator 224 to create fourth water stream 226 and fourth dehydrated formalin stream 228. Both second and third dehydrated formalin streams 216 and 222, respectively, are preferably fed to the middle portions of third and fourth evaporators 218 and 224, respectively, however, in other embodiments, the dehydrated formalin streams may be fed at other positions of the evaporators. In one embodiment, the temperature of the third and fourth dehydrated stream ranges from 20° C. to 100° C., e.g., from 30° C. to 80° C., from 45° C. to 70° C., or from 50° C. to 65° C. In one embodiment, the pressure at which the third and fourth evaporators are operated may range from 1 kPa to 300 kPa, e.g., from 5 kPa to 100 kPa, or from 10 kPa to 50 kPa.

Exemplary compositional ranges for the third water stream and the third dehydrated formalin stream of third evaporator 218 are shown in Table 4. Components other than those listed in Table 4 may also be present in the water stream and the dehydrated formalin stream.

TABLE 4

THIRD EVAPORATOR

|  | Conc. (wt. %) | Conc. (wt. %) | Conc. (wt. %) |
|---|---|---|---|
| Third Water Stream | | | |
| Water | 25 to 90 | 35 to 75 | 45 to 60 |
| Formaldehyde | 15 to 60 | 30 to 55 | 40 to 50 |
| Methanol | <3 | <1 | <0.5 |
| Third Dehydrated Stream | | | |
| Formaldehyde | 50 to 95 | 60 to 85 | 70 to 80 |
| Water | 10 to 40 | 15 to 35 | 20 to 30 |
| Methanol | <2 | <1 | <1 |

Exemplary compositional ranges for the fourth water stream and the fourth dehydrated formalin stream of fourth evaporator 224 are shown in Table 5. Components other than those listed in Table 5 may also be present in the water stream and the dehydrated stream.

TABLE 5

FOURTH EVAPORATOR

|  | Conc. (wt. %) | Conc. (wt. %) | Conc. (wt. %) |
|---|---|---|---|
| Fourth Water Stream | | | |
| Water | 20 to 85 | 30 to 65 | 40 to 55 |
| Formaldehyde | 30 to 70 | 40 to 65 | 50 to 60 |
| Methanol | <3 | <1 | <0.5 |
| Fourth Dehydrated Stream | | | |
| Formaldehyde | 50 to 95 | 60 to 85 | 70 to 80 |
| Water | 10 to 40 | 15 to 35 | 20 to 30 |
| Methanol | <2 | <1 | <1 |

In an embodiment, the dehydration process 202 preferably removes more than 30 wt. % of water from formalin, e.g., more than 50 wt. %, more than 75 wt. % or more than 80 wt. %. In an embodiment, the dehydration process 202 removes at most 5 wt. % of the formaldehyde from formalin, e.g., at most 20 wt. %, at most 30 wt. %, or at most 35 wt. %. In an embodiment, the dehydration process 202 removes at least 60 wt. % of the methanol from formalin, e.g., at least 80 wt. %, at least 90 wt. %, or at least 98 wt. %.

In an embodiment, the last dehydrated formalin stream, i.e., the stream being fed to the reactor via a vaporizer, preferably comprises at least 60 wt. % formaldehyde, e.g., at least 70 wt. %, at least 80 wt. % or at least 85 wt. %. In an embodiment, the last dehydrated formalin stream comprises at most 35 wt. % water, at most 25 wt. %, or at most 15 wt. %.

Figure 3:
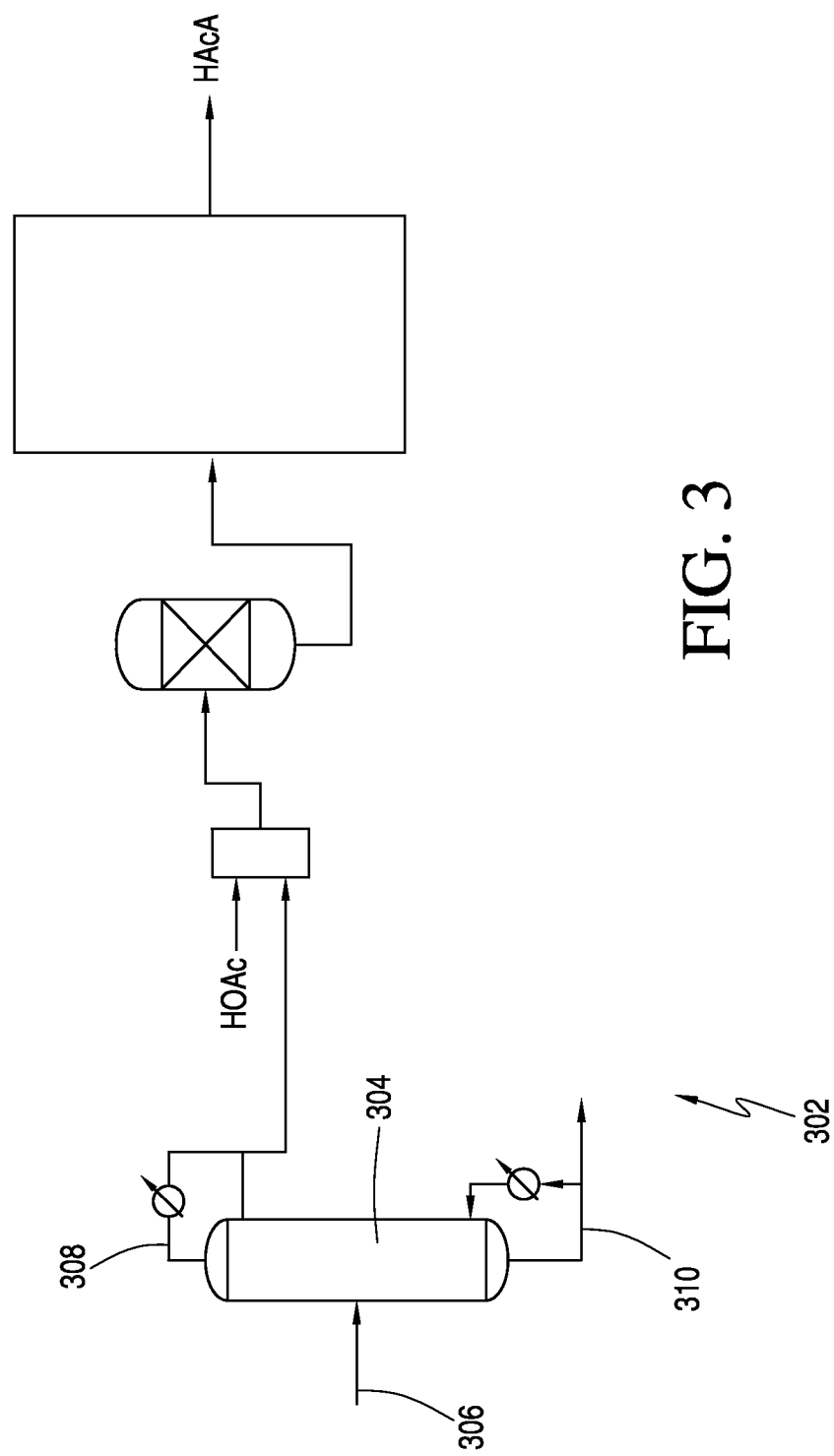
FIG. 3 is a schematic diagram of an acrylic acid reaction/separation system in accordance with one embodiment of the present invention.

FIG. 3 shows one embodiment of a formalin dehydration, reaction and separation scheme in accordance with the present invention. As shown in FIG. 3, dehydration zone 302 comprises at least one water removal unit, e.g., distillation column 304. In an embodiment, formalin in line 306 is fed to distillation column 304. Distillation column 304 forms distillate stream 308 comprising formaldehyde and residue stream 310 comprising water. The distillate stream may be refluxed and the residue stream may be boiled up as shown.

In an embodiment, distillate stream 308 comprises at least 55 wt. % formaldehyde, e.g., at least 60 wt. % or at least 65 wt. %. In terms of ranges, the distillate stream 308 comprises from 55 wt. % to 95 wt. % formaldehyde, e.g., from 60 wt. % to 85 wt. %, or from 65 wt. % to 75 wt. %. In an embodiment, distillate stream 308 comprises less than 45 wt. % water, e.g., less than 40 wt. %, less than 35 wt. %, or less than 30 wt. %.

In an embodiment, residue stream 310 comprises at least 45 wt. % water, at least 60 wt. %, at least 80 wt. %, or at least 95 wt. %. In an embodiment, residue stream 310 comprises less than 30 wt. % formaldehyde, e.g., less than 15 wt. %, less than 10 wt. %, or less than 5 wt. %.

In one embodiment, the temperature of crude formalin in line 306 ranges from 20° C. to 100° C., e.g., from 20° C. to 70° C., from 30° C. to 55° C., or from 35° C. to 50° C. In one embodiment, the pressure of the crude formalin in line 306 is preferably from 300 kPa to 1000 kPa, e.g., from 450 kPa to 900 kPa, or from 600 kPa to 700 kPa.

In one embodiment, the temperature of the dehydrated formaldehyde distillate exiting the distillation column ranges from 75° C. to 200° C., e.g., from 90° C. to 175° C., from 120° C. to 160° C. or from 140° C. to 150° C. In one embodiment, the temperature of the water residue exiting the distillation column ranges from 75° C. to 215° C., e.g., from 100° C. to 185° C., from 130° C. to 170° C. or from 150° C. to 160° C.

In one embodiment, the distillation column may be operated at a pressure range from 300 kPa to 1000 kPa, e.g., from 450 kPa to 900 kPa or from 600 kPa to 700 kPa. In a preferred embodiment, the distillate in line 308 is refluxed as showed, for example, at a reflux ratio of from 1:30 to 30:1, e.g., from 1:5 to 5:1 or from 1:3 to 3:1.

Exemplary compositional ranges for the distillate and residue of dehydration column column 304 are shown in Table 6. Components other than those listed in Table 6 may also be present in the residue and distillate.

TABLE 6

DEHYDRATION COLUMN

|  | Conc. (wt. %) | Conc. (wt. %) | Conc. (wt. %) |
|---|---|---|---|
| Distillate | | | |
| Water | 15 to 80 | 20 to 60 | 30 to 40 |
| Formaldehyde | 30 to 95 | 50 to 80 | 60 to 70 |
| Methanol | Undetected | Undetected | Undetected |
| Residue | | | |
| Formaldehyde | 5 to 30 | 5 to 10 | <5 |
| Water | >90 | >95 | >99 |
| Methanol | Undetected | Undetected | Undetected |

As shown in FIG. 2 and FIG. 3, the dehydrated formalin streams 228 and 308, respectively, and acetic acid are fed to a vaporizer to create a vapor feed stream. The vapor feed stream is then fed to a reactor to make the acrylate product.

Separation

Figure 4:
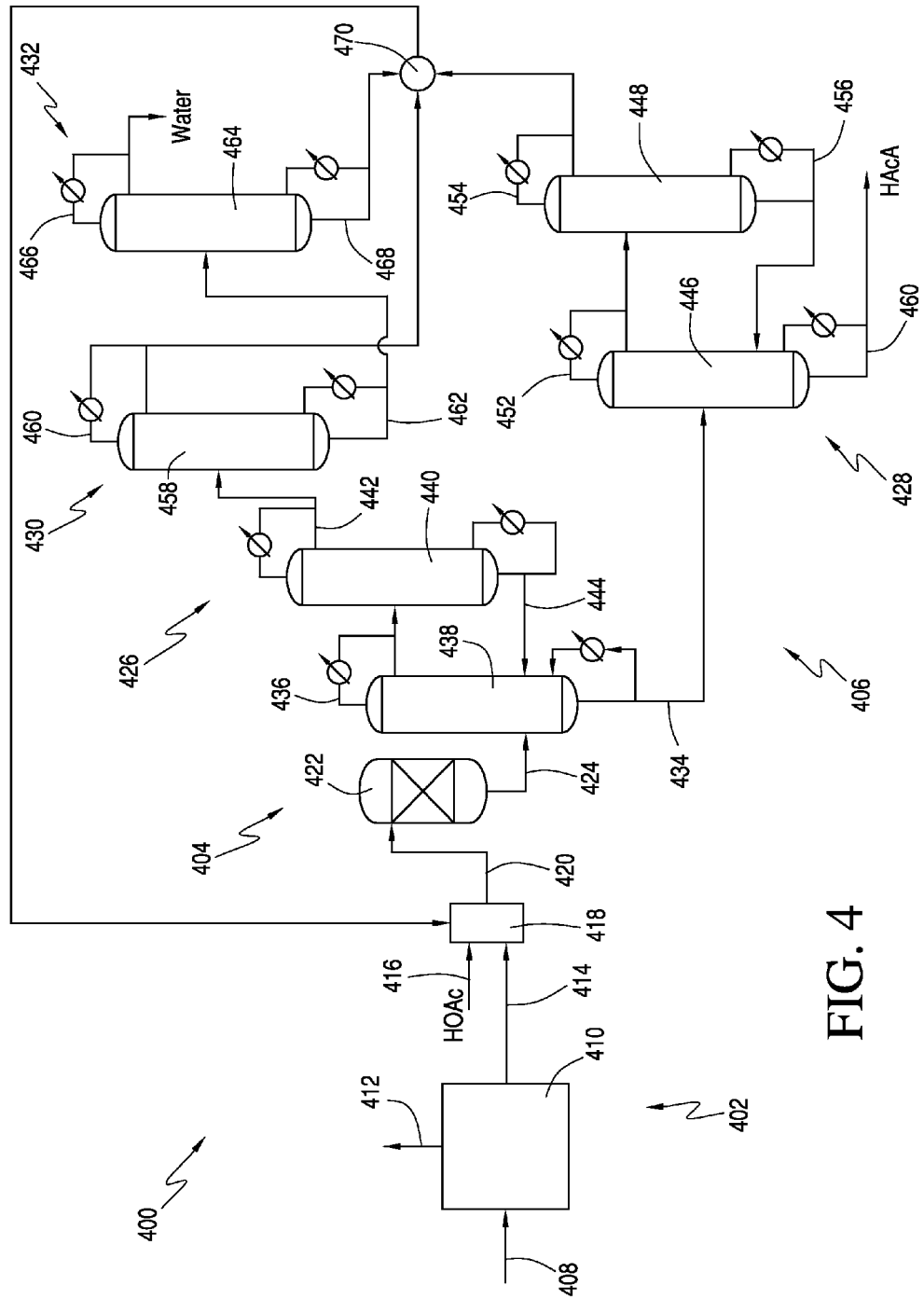
FIG. 4 is a schematic diagram of an acrylic acid reaction/separation system in accordance with one embodiment of the present invention.

FIG. 4 shows an embodiment of reaction and separation scheme using a dehydrated formalin stream in accordance with the present invention. As shown in FIG. 4, acrylate product system 400 comprises dehydration zone 402, reaction zone 404, and purification zone 406. In dehydration zone 402, crude formalin in line 408 is fed to dehydration unit 410 to form a water stream in line 412 and a dehydrated formalin stream in line 414. Acetic acid and dehydrated formalin are fed to vaporizer 418 via lines 416 and 414, respectively. Vaporizer 418 creates a vapor feed stream, which exits vaporizer 418 via line 420 and is directed to reactor 422. In one embodiment, lines 414 and 416 may be combined and jointly fed to the vaporizer 418. The temperature of the vapor feed stream in line 420 is preferably from 200° C. to 600° C., e.g., from 250° C. to 500° C. or from 340° C. to 425° C. Alternatively, a vaporizer may not be employed and the reactants may be fed directly to reactor 422.

Any feed that is not vaporized may be removed from vaporizer 418 and may be recycled or discarded. In addition, although line 420 is shown as being directed to the upper half of reactor 422, line 420 may be directed to the middle or bottom of reactor 422. Further modifications and additional components to reaction zone 404 and purification zone 406 are described below.

Purification zone 406 comprises alkylenating agent split unit 426, acrylate product split unit 428, acetic acid split unit 430, and drying unit 432. Purification zone 406 may also comprise an optional light ends removal unit (not shown). For example, the light ends removal unit may comprise a condenser and/or a flasher. The light ends removal unit may be configured either upstream or downstream of the alkylenating agent split unit. Depending on the configuration, the light ends removal unit removes light ends from the crude product stream, the alkylenating stream, and/or the intermediate acrylate product stream. In one embodiment, when the light ends are removed, the remaining liquid phase comprises the acrylic acid, acetic acid, alkylenating agent, and/or water.

Reactor 422 contains the catalyst that is used in the reaction to form crude product stream, which is withdrawn, preferably continuously, from reactor 422 via line 424. Although FIG. 4 shows the crude product stream being withdrawn from the bottom of reactor 422, the crude product stream may be withdrawn from any portion of reactor 422. Exemplary composition ranges for the crude product stream are shown in Table 1 above.

In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

The crude product stream in line 424 is fed to alkylenating agent split unit 426. Alkylenating agent split unit 426 may comprise one or more separation units, e.g., two or more or three or more. In one example, the alkylenating agent split unit contains multiple columns, as shown in FIG. 4. Alkylenating agent split unit 426 separates the crude product stream into at least one intermediate acrylate product stream, which exits via line 434 and at least one alkylenating agent stream, which exits via line 436. Exemplary compositional ranges for the intermediate acrylate product stream are shown in Table 7. Components other than those listed in Table 7 may also be present in the intermediate acrylate product stream. Examples include methanol, methyl acetate, methyl acrylate, dimethyl ketone, carbon dioxide, carbon monoxide, oxygen, nitrogen, and acetone.

TABLE 7

INTERMEDIATE ACRYLATE PRODUCT STREAM COMPOSITION

| | Conc. (wt. %) | Conc. (wt. %) | Conc. (wt. %) |
|---|---|---|---|
| Acrylic Acid | at least 5 | 5 to 99 | 35 to 65 |
| Acetic Acid | less than 95 | 5 to 90 | 20 to 60 |
| Water | less than 25 | less than 10 | less than 1 |
| Alkylenating Agent | <1 | <0.5 | <0.1 |
| Propionic Acid | <10 | 0.01 to 5 | 0.01 to 1 |

In other embodiments, the intermediate acrylate product stream comprises higher amounts of alkylenating agent. For example, the intermediate acrylate product stream may comprise from 1 wt. % to 10 wt. % alkylenating agent, e.g., from 1 wt. % to 8 wt. % or from 2 wt. % to 5 wt. %. In one embodiment, the intermediate acrylate product stream comprises greater than 1 wt. % alkylenating agent, e.g., greater than 5 wt. % or greater than 10 wt. %.

Exemplary compositional ranges for the alkylenating agent stream are shown in Table 8. Components other than those listed in Table 8 may also be present in the purified alkylate product stream. Examples include methanol, methyl acetate, methyl acrylate, dimethyl ketone, carbon dioxide, carbon monoxide, oxygen, nitrogen, and acetone.

TABLE 8

ALKYLENATING AGENT STREAM COMPOSITION

| | Conc. (wt. %) | Conc. (wt. %) | Conc. (wt. %) |
|---|---|---|---|
| Acrylic Acid | less than 25 | 0.01 to 15 | 0.1 to 10 |
| Acetic Acid | 10 to 65 | 20 to 65 | 25 to 55 |
| Water | 5 to 75 | 10 to 60 | 20 to 40 |
| Alkylenating Agent | at least 1 | 1 to 75 | 10 to 20 |
| Propionic Acid | <10 | 0.001 to 5 | 0.001 to 1 |

In other embodiments, the alkylenating stream comprises lower amounts of acetic acid. For example, the alkylenating agent stream may comprise less than 10 wt. % acetic acid, e.g., less than 5 wt. % or less than 1 wt. %.

As mentioned above, the crude product stream of the present invention comprises little, if any, furfural and/or acrolein. As such the derivative stream(s) of the crude product streams will comprise little, if any, furfural and/or acrolein. In one embodiment, the derivative stream(s), e.g., the streams of the separation zone, comprises less than less than 500 wppm acrolein, e.g., less than 100 wppm, less than 50 wppm, or less than 10 wppm. In one embodiment, the derivative stream(s) comprises less than less than 500 wppm furfural, e.g., less than 100 wppm, less than 50 wppm, or less than 10 wppm.

Alkylenating agent split unit 426 may comprise any suitable separation device or combination of separation devices. For example, alkylenating agent split unit 426 may comprise a column, e.g., a standard distillation column, an extractive distillation column and/or an azeotropic distillation column. In other embodiments, alkylenating agent split unit 426 comprises a precipitation unit, e.g., a crystallizer and/or a chiller. Preferably, alkylenating agent split unit 426 comprises two standard distillation columns. In another embodiment, the alkylenating agent split is performed by contacting the crude product stream with a solvent that is immiscible with water. For example alkylenating agent split unit 426 may comprise at least one liquid-liquid extraction columns. In another embodiment, the alkylenating agent split is performed via azeotropic distillation, which employs an azeotropic agent. In these cases, the azeotropic agent may be selected from the group consisting of methyl isobutylketene, o-xylene, toluene, benzene, n-hexane, cyclohexane, p-xylene, and mixtures thereof. This listing is not exclusive and is not meant to limit the scope of the invention. In another embodiment, the alkylenating agent split is performed via a combination of distillation, e.g., standard distillation, and crystallization. Of course, other suitable separation devices may be employed either alone or in combination with the devices mentioned herein.

In FIG. 4, alkylenating agent split unit 426 comprises first column 438 and second column 440. Alkylenating agent split unit 426 receives crude acrylic product stream in line 424 and separates same into at least one alkylenating agent stream, e.g., stream 442, and at least one intermediate product stream, e.g., stream 434. Alkylenating agent split unit 426 performs an alkylenating agent split, as discussed above.

In operation, as shown in FIG. 4, the crude product stream in line 424 is directed to first column 438. First column 424 separates the crude product stream a distillate in line 436 and a residue in line 434. The distillate may be refluxed and the residue may be boiled up as shown. Stream 436 comprises at least 1 wt. % alkylenating agent. As such, stream 436 may be considered an alkylenating agent stream. The first column residue exits first column 438 in line 434 and comprises a significant portion of acrylate product. As such, stream 434 is an intermediate product stream. Exemplary compositional ranges for the distillate and residue of first column 438 are shown in Table 9. Components other than those listed in Table 4 may also be present in the residue and distillate.

TABLE 9

FIRST COLUMN

|  | Conc. (wt. %) | Conc. (wt. %) | Conc. (wt. %) |
|---|---|---|---|
| Distillate |  |  |  |
| Acrylic Acid | 0.01 to 20 | 0.01 to 15 | 0.1 to 10 |
| Acetic Acid | 25 to 75 | 35 to 65 | 45 to 55 |
| Water | 5 to 75 | 10 to 60 | 20 to 40 |
| Alkylenating Agent | at least 1 | 1 to 75 | 10 to 20 |
| Propionic Acid | <10 | 0.001 to 5 | 0.001 to 1 |
| Residue |  |  |  |
| Acrylic Acid | at least 5 | 5 to 99 | 35 to 65 |
| Acetic Acid | less than 95 | 5 to 90 | 20 to 60 |
| Water | less than 25 | less than 10 | less than 1 |
| Alkylenating Agent | <1 | <0.5 | <0.1 |
| Propionic Acid | <10 | 0.01 to 5 | 0.01 to 1 |

In one embodiments, the first distillate comprises smaller amounts of acetic acid, e.g., less than 25 wt. %, less than 10 wt. %, less than 5 wt. % or less than 1 wt. %. In one embodiment, the first residue comprises larger amounts of alkylenating agent.

In other embodiments, the intermediate acrylate product stream comprises higher amounts of alkylenating agent, e.g., greater than 1 wt. % greater than 5 wt. % or greater than 10 wt. %.

For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

In one embodiment, polymerization inhibitors and/or anti-foam agents may be employed in the separation zone, e.g., in the units of the separation zone. The inhibitors may be used to reduce the potential for fouling caused by polymerization of acrylates. The anti-foam agents may be used to reduce potential for foaming in the various streams of the separation zone. The polymerization inhibitors and/or the anti-foam agents may be used at one or more locations in the separation zone.

Returning to FIG. 4, at least a portion of stream 436 is directed to second column 440. Second column 440 separates the at least a portion of stream 436 into a distillate in line 442 and a residue in line 444. The distillate may be refluxed and the residue may be boiled up as shown. The distillate comprises at least 1 wt. % alkylenating agent. Stream 442, like stream 436, may be considered an alkylenating agent stream. The second column residue exits second column 440 in line 444 and comprises a significant portion of acetic acid. At least a portion of line 444 may be returned to first column 438 for further separation. In one embodiment, at least a portion of line 444 is returned, either directly or indirectly, to reactor 422. Exemplary compositional ranges for the distillate and residue of second column 440 are shown in Table 5. Components other than those listed in Table 10 may also be present in the residue and distillate.

TABLE 10

SECOND COLUMN

|  | Conc. (wt. %) | Conc. (wt. %) | Conc. (wt. %) |
|---|---|---|---|
| Distillate |  |  |  |
| Acrylic Acid | 0.01 to 10 | 0.05 to 5 | 0.1 to 0.5 |
| Acetic Acid | 10 to 70 | 30 to 60 | 40 to 50 |
| Water | 10 to 70 | 30 to 60 | 40 to 50 |
| Alkylenating Agent | at least 1 | 1 to 75 | 10 to 20 |
| Propionic Acid | 0.01 to 10 | 0.01 to 5 | 0.01 to 0.05 |
| Residue |  |  |  |
| Acrylic Acid | 0.1 to 45 | 5 to 35 | 10 to 20 |
| Acetic Acid | 30 to 80 | 40 to 70 | 50 to 60 |
| Water | 1 to 40 | 5 to 35 | 10 to 20 |
| Alkylenating Agent | at least 1 | 1 to 75 | 10 to 20 |
| Propionic Acid | <10 | 0.001 to 5 | 0.001 to 1 |

In cases where any of the alkylenating agent split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 100 kPa, less than 80 kPa, or less than 60 kPa. In terms of lower limits, the column(s) may be operated at a pressures of at least 1 kPa, e.g., at least 20 kPa or at least 40 kPa. Without being bound by theory, it is believed that alkylenating agents, e.g., formaldehyde, may not be sufficiently volatile at lower pressures. Thus, maintenance of the column pressures at these levels surprisingly and unexpectedly provides for efficient separation operations. In addition, it has surprisingly and unexpectedly been found that by maintaining a low pressure in the columns of alkylenating agent split unit 436 may inhibit and/or eliminate polymerization of the acrylate products, e.g., acrylic acid, which may contribute to fouling of the column(s).

In one embodiment, the alkylenating agent split is achieved via one or more liquid-liquid extraction units. Preferably, the one or more liquid-liquid extraction units employ one or more extraction agents. Multiple liquid-liquid extraction units may be employed to achieve the alkylenating agent split. Any suitable liquid-liquid extraction devices used for multiple equilibrium stage separations may be used. Also, other separation devices, e.g., traditional columns, may be employed in conjunction with the liquid-liquid extraction unit(s).

In one embodiment (not shown), the crude product stream is fed to a liquid-liquid extraction column where the crude product stream is contacted with an extraction agent, e.g., an organic solvent. The liquid-liquid extraction column extracts the acids, e.g., acrylic acid and acetic acid, from the crude product stream. An aqueous stage comprising water, alkylenating agent, and some acetic acid exits the liquid-liquid extraction unit. Small amounts of acrylic acid may also be present in the aqueous stream. The aqueous phase may be further treated and/or recycled. An organic phase comprising acrylic acid, acetic acid, and the extraction agent also exits the liquid-liquid extraction unit. The organic phase may also comprise water and formaldehyde. The acrylic acid may be separated from the organic phase and collected as product. The acetic acid may be separated then recycled and/or used elsewhere. The solvent may be recovered and recycled to the liquid-liquid extraction unit.

The inventive process further comprises the step of separating the intermediate acrylate product stream to form a finished acrylate product stream and a first finished acetic acid stream. The finished acrylate product stream comprises acrylate product(s) and the first finished acetic acid stream comprises acetic acid. The separation of the acrylate products from the intermediate product stream to form the finished acrylate product may be referred to as the "acrylate product split."

Returning to FIG. 4, intermediate product stream 434 exits alkylenating agent split unit 426 and is directed to acrylate product split unit 428 for further separation, e.g., to further separate the acrylate products therefrom. Acrylate product split unit 428 may comprise any suitable separation device or combination of separation devices. For example, acrylate product split unit 428 may comprise at least one column, e.g., a standard distillation column, an extractive distillation column and/or an azeotropic distillation column. In other embodiments, acrylate product split unit 428 comprises a precipitation unit, e.g., a crystallizer and/or a chiller. Preferably, acrylate product split unit 428 comprises two standard distillation columns as shown in FIG. 4. In another embodiment, acrylate product split unit 428 comprises a liquid-liquid extraction unit. Of course, other suitable separation devices may be employed either alone or in combination with the devices mentioned herein.

In FIG. 4, acrylate product split unit 428 comprises third column 446 and fourth column 448. Acrylate product split unit 428 receives at least a portion of intermediate acrylic product stream in line 434 and separates same into purified acrylate product stream 450 and at least one acetic acid-containing stream. As such, acrylate product split unit 428 may yield the finished acrylate product.

As shown in FIG. 4, at least a portion of intermediate acrylic product stream in line 434 is directed to third column 446. Third column 446 separates the intermediate acrylic product stream to form third distillate, e.g., line 452, and third residue, which is the finished acrylate product stream, e.g., line 450. The distillate may be refluxed and the residue may be boiled up as shown.

Stream 452 comprises acetic acid and some acrylic acid. The third column residue exits third column 446 in line 450 and comprises a significant portion of acrylate product. As such, stream 450 is a finished product stream. Exemplary compositional ranges for the distillate and residue of third column 446 are shown in Table 11. Components other than those listed in Table 11 may also be present in the residue and distillate.

TABLE 11

THIRD COLUMN

| | Conc. (wt. %) | Conc. (wt. %) | Conc. (wt. %) |
|---|---|---|---|
| Distillate | | | |
| Acrylic Acid | 0.1 to 45 | 1 to 40 | 5 to 35 |
| Acetic Acid | 60 to 99 | 60 to 90 | 65 to 75 |
| Water | 0.1 to 25 | 0.1 to 10 | 1 to 5 |
| Alkylenating Agent | <1 | 0.001 to 1 | 0.1 to 1 |
| Propionic Acid | <10 | 0.001 to 5 | 0.001 to 1 |
| Residue | | | |
| Acrylic Acid | at least 85 | 85 to 99.9 | 95 to 99.5 |
| Acetic Acid | <15 | 0.1 to 10 | 0.1 to 5 |
| Water | <1 | <0.1 | <0.01 |
| Alkylenating Agent | <1 | 0.001 to 1 | 0.1 to 1 |
| Propionic Acid | 0.1 to 10 | 0.1 to 5 | 0.5 to 3 |

Returning to FIG. 4, at least a portion of stream 452 is directed to fourth column 448. Fourth column 448 separates the at least a portion of stream 452 into a distillate in line 454 and a residue in line 456. The distillate may be refluxed and the residue may be boiled up as shown. The distillate comprises a major portion of acetic acid. In one embodiment, at least a portion of line 454 is returned, either directly or indirectly, to reactor 422. The fourth column residue exits fourth column 448 in line 456 and comprises acetic acid and some acrylic acid. At least a portion of line 456 may be returned to third column 446 for further separation. In one embodiment, at least a portion of line 456 is returned, either directly or indirectly, to reactor 422. In another embodiment, at least a portion of the acetic acid-containing stream in either or both of lines 454 and 456 may be directed to an ethanol production system that utilizes the hydrogenation of acetic acid form the ethanol. Exemplary compositional ranges for the distillate and residue of fourth column 448 are shown in Table 12. Components other than those listed in Table 12 may also be present in the residue and distillate.

TABLE 12

FOURTH COLUMN

| | Conc. (wt. %) | Conc. (wt. %) | Conc. (wt. %) |
|---|---|---|---|
| Distillate | | | |
| Acrylic Acid | 0.01 to 10 | 0.05 to 5 | 0.1 to 1 |
| Acetic Acid | 50 to 99.9 | 70 to 99.5 | 80 to 99 |
| Water | 0.1 to 25 | 0.1 to 15 | 1 to 10 |
| Alkylenating Agent | <10 | 0.001 to 5 | 0.01 to 5 |
| Propionic Acid | 0.0001 to 10 | 0.001 to 5 | 0.001 to 0.05 |
| Residue | | | |
| Acrylic Acid | 5 to 75 | 15 to 60 | 30 to 50 |
| Acetic Acid | 30 to 95 | 40 to 80 | 50 to 75 |

TABLE 12-continued

FOURTH COLUMN

| | Conc. (wt. %) | Conc. (wt. %) | Conc. (wt. %) |
|---|---|---|---|
| Water | 0.01 to 10 | 0.01 to 5 | 0.1 to 1 |
| Alkylenating Agent | <1 | 0.001 to 1 | 0.1 to 1 |
| Propionic Acid | <10 | 0.001 to 5 | 0.001 to 1 |

In cases where the acrylate product split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 50 kPa, less than 27 kPa, or less than 20 kPa. In terms of lower limits, the column(s) may be operated at a pressures of at least 1 kPa, e.g., at least 3 kPa or at least 5 kPa. Without being bound by theory, it has surprisingly and unexpectedly been found that be maintaining a low pressure in the columns of acrylate product split unit 428 may inhibit and/or eliminate polymerization of the acrylate products, e.g., acrylic acid, which may contribute to fouling of the column(s).

It has also been found that, surprisingly and unexpectedly, maintaining the temperature of acrylic acid-containing streams fed to acrylate product split unit 428 at temperatures below 140° C., e.g., below 130° C. or below 115° C., may inhibit and/or eliminate polymerization of acrylate products. In one embodiment, to maintain the liquid temperature at these temperatures, the pressure of the column(s) is maintained at or below the pressures mentioned above. In these cases, due to the lower pressures, the number of theoretical column trays is kept at a low level, e.g., less than 10, less than 8, less than 7, or less than 5. As such, it has surprisingly and unexpectedly been found that multiple columns having fewer trays inhibit and/or eliminate acrylate product polymerization. In contrast, a column having a higher amount of trays, e.g., more than 10 trays or more than 15 trays, would suffer from fouling due to the polymerization of the acrylate products. Thus, in a preferred embodiment, the acrylic acid split is performed in at least two, e.g., at least three, columns, each of which have less than 10 trays, e.g. less than 7 trays. These columns each may operate at the lower pressures discussed above.

The inventive process further comprises the step of separating an alkylenating agent stream to form a purified alkylenating stream and a purified acetic acid stream. The purified alkylenating agent stream comprises a significant portion of alkylenating agent, and the purified acetic acid stream comprises acetic acid and water. The separation of the alkylenating agent from the acetic acid may be referred to as the "acetic acid split."

Returning to FIG. 4, alkylenating agent stream 442 exits alkylenating agent split unit 426 and is directed to acetic acid split unit 430 for further separation, e.g., to further separate the alkylenating agent and the acetic acid therefrom. Acetic acid split unit 430 may comprise any suitable separation device or combination of separation devices. For example, acetic acid split unit 430 may comprise at least one column, e.g., a standard distillation column, an extractive distillation column and/or an azeotropic distillation column. In other embodiments, acetic acid split unit 430 comprises a precipitation unit, e.g., a crystallizer and/or a chiller. Preferably, acetic acid split unit 430 comprises a standard distillation column as shown in FIG. 4. In another embodiment, acetic acid split unit 430 comprises a liquid-liquid extraction unit. Of course, other suitable separation devices may be employed either alone or in combination with the devices mentioned herein.

In FIG. 4, acetic acid split unit 430 comprises fifth column 458. Acetic acid split unit 430 receives at least a portion of alkylenating agent stream in line 442 and separates same into a fifth distillate comprising alkylenating agent in line 460, e.g., a purified alkylenating stream, and a fifth residue comprising acetic acid in line 462, e.g., a purified acetic acid stream. The distillate may be refluxed and the residue may be boiled up as shown. In one embodiment, at least a portion of line 460 and/or line 462 are returned, either directly or indirectly, to reactor 422. At least a portion of stream in line 462 may be further separated. In another embodiment, at least a portion of the acetic acid-containing stream in line 462 may be directed to an ethanol production system that utilizes the hydrogenation of acetic acid form the ethanol.

The stream in line 460 comprises alkylenating agent and water. The stream in line 462 comprises acetic acid and water. Exemplary compositional ranges for the distillate and residue of fifth column 458 are shown in Table 13. Components other than those listed in Table 13 may also be present in the residue and distillate.

TABLE 13

FIFTH COLUMN

| | Conc. (wt. %) | Conc. (wt. %) | Conc. (wt. %) |
|---|---|---|---|
| Distillate | | | |
| Acrylic Acid | <1 | 0.001 to 5 | 0.001 to 1 |
| Acetic Acid | <1 | 0.001 to 5 | 0.001 to 1 |
| Water | 40 to 80 | 50 to 70 | 55 to 65 |
| Alkylenating Agent | 20 to 60 | 30 to 50 | 35 to 45 |
| Propionic Acid | <1 | 0.001 to 5 | 0.001 to 1 |
| Residue | | | |
| Acrylic Acid | <1 | 0.01 to 5 | 0.1 to 1 |
| Acetic Acid | 25 to 95 | 45 to 85 | 60 to 70 |
| Water | 15 to 75 | 25 to 65 | 30 to 40 |
| Alkylenating Agent | <1 | 0.01 to 5 | 0.1 to 1 |
| Propionic Acid | <1 | 0.001 to 5 | 0.001 to 1 |

In cases where the acetic acid split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

The inventive process further comprises the step of separating the purified acetic acid stream to form a second finished acetic acid stream and a water stream. The second finished acetic acid stream comprises a major portion of acetic acid, and the water stream comprises mostly water. The separation of the acetic from the water may be referred to as dehydration.

Returning to FIG. 4, fifth residue 462 exits acetic acid split unit 430 and is directed to drying unit 432 for further separation, e.g., to remove water from the acetic acid. Drying unit 432 may comprise any suitable separation device or combination of separation devices. For example, drying unit 432 may comprise at least one column, e.g., a standard distillation column, an extractive distillation column and/or an azeotropic distillation column. In other embodiments, drying unit 432 comprises a dryer and/or a molecular sieve unit. In a preferred embodiment, drying unit 432 comprises a liquid-liquid extraction unit. In one embodiment, drying unit 432 comprises a standard distillation column as shown in FIG. 4. Of course, other suitable separation devices may be employed either alone or in combination with the devices mentioned herein.

In FIG. 4, drying unit 432 comprises sixth column 464. Drying unit 432 receives at least a portion of second finished acetic acid stream in line 462 and separates same into a sixth distillate comprising a major portion of water in line 466 and a sixth residue comprising acetic acid and small amounts of water in line 468. The distillate may be refluxed and the residue may be boiled up as shown. In one embodiment, at least a portion of line 468 is returned, either directly or indirectly, to reactor 422. In another embodiment, at least a portion of the acetic acid-containing stream in line 468 may be directed to an ethanol production system that utilizes the hydrogenation of acetic acid form the ethanol.

Exemplary compositional ranges for the distillate and residue of sixth column 464 are shown in Table 14. Components other than those listed in Table 14 may also be present in the residue and distillate.

TABLE 14

SIXTH COLUMN

| | Conc. (wt. %) | Conc. (wt. %) | Conc. (wt. %) |
|---|---|---|---|
| Distillate | | | |
| Acrylic Acid | <1 | 0.001 to 5 | 0.001 to 1 |
| Acetic Acid | <1 | 0.01 to 5 | 0.01 to 1 |
| Water | 90 to 99.9 | 95 to 99.9 | 95 to 99.5 |
| Alkylenating Agent | <1 | 0.01 to 5 | 0.01 to 1 |
| Propionic Acid | <1 | 0.001 to 5 | 0.001 to 1 |
| Residue | | | |
| Acrylic Acid | <1 | 0.01 to 5 | 0.01 to 1 |
| Acetic Acid | 75 to 99.9 | 85 to 99.5 | 90 to 99.5 |
| Water | 0.01 to 55 | 0.01 to 25 | 0.01 to 10 |
| Alkylenating Agent | <1 | <0.001 | <0.0001 |
| Propionic Acid | <1 | 0.001 to 5 | 0.001 to 1 |

In cases where the drying unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa. FIG. 4 also shows tank 470, which, collects at least one of the process streams prior to recycling same to reactor 422. Tank 470 is an optional feature. The various recycle streams that may, alternatively, be recycled directly to reactor 422 without being collected in tank 470.

EXAMPLES

Example 1

Figure 5:
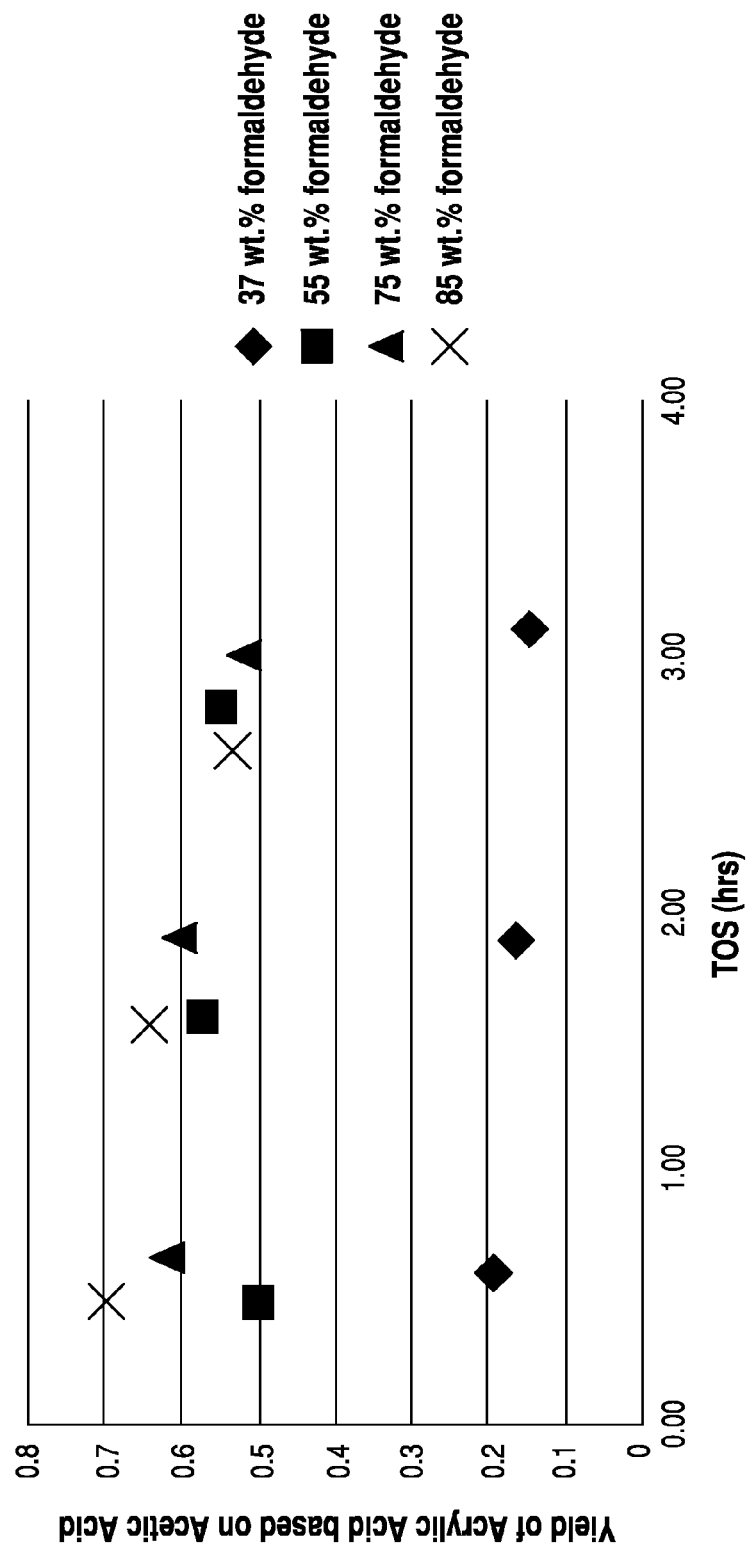
FIG. 5 is a chart illustrating the yields of acrylic acid by using different concentrations of formalin.

FIG. 5 is a graph showing the yields of acrylic acid using different concentrations of formaldehyde as starting materials. Different concentrations of formalin (water and formaldehyde) were prepared by removing water from the crude formalin stream. The reactions were carried out at 370° C. and $V_2Ti_4$ was used as a reference catalyst. The mass feed ratio for the reactions was 1 and the molar feed ratio was 0.5. For all reactions, 1 mol. % $O_2$, 10.5 mol. % HOAc, 21 mol. %, HCHO were used. In FIG. 5, the $N_2:H_2O$ mol. % ratio was 10:58.5 for the 37 wt. % formalin case, 40:28.5 for the 55 wt. % formalin case, 55:13.5 for the 75 wt. % formalin case, and 61:7.5 for the 85 wt. % formalin case.

The reaction of formaldehyde and acetic acid was conducted using a formalin composition comprising various levels of formaldehyde, e.g., 37 wt. % formaldehyde, 55 wt. % formaldehyde, and 75 wt. % formaldehyde, and 85 wt. % formaldehyde. For these formalin compositions, the remainder of the stream comprised primarily water along with small amounts of methanol. For each formalin concentration, the yields of acrylic acid were calculated based on the amount of acetic acid used in the aldol condensation reaction. The results are shown in FIG. 5.

As shown in FIG. 5, at low concentration of formaldehyde, e.g., 37 wt. %, the yield of acrylic acid was about 20% within the first hour of the reaction and gradually decreased to about 15% at the third hour. Surprisingly and unexpectedly, by removing 45 wt. % of water from formalin, i.e., 55 wt. % formaldehyde, the acrylic acid yield increased to 50% within the first hour. The acrylic acid yield further improved to close to 60% at the second hour and lowered slightly to around 55% at the third hour.

In comparison, when additional water is removed, the acrylic acid further improved during the first hour of the reaction. As shown in FIG. 5, by using 75 wt. % and 85 wt. % formaldehyde in the aldol condensation reaction, the yields of acrylic acid improved to 60% and 70%, respectively. Surprisingly and unexpectedly, the yields of acrylic acid using 75 wt. % and 85 wt. % formaldehyde decreased as the reaction entered the second hour. The yields further decreased to less than 60% as the reaction reached the third hour. Thus, the data shows that the yield of acrylic acid greatly improves by removing water from formalin. Surprisingly and unexpectedly, the yield of acrylic acid greatly improved in the first hour of the reaction when a large amount of water is removed from the formalin starting material. For example, by using 85 wt. % formaldehyde instead of 37 wt. % formaldehyde for the aldol condensation reaction, the yield of acrylic acid increased from below 20% to about 70%.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an acrylate product, comprising the steps of:
    dehydrating a crude alkylenating agent stream comprising alkylenating agent and water to form a dehydrated alkylenating agent stream comprising less than 35 wt % water and a water stream;
    reacting acetic acid with at least a portion of the dehydrated alkylenating agent stream to form a crude acrylate product stream comprising acrylate product, and alkylenating agent, and acetic acid;
    distilling at least a portion of the crude acrylate product stream to form an overhead comprising an alkylenating agent stream comprising at least 5 wt % alkylenating agent and a residue comprising an intermediate product stream comprising acrylate product and acetic acid; and
    separating the intermediate product stream to form a finished acrylate product stream comprising at least 85 wt % acrylic acid and a first finished acetic acid stream comprising from 50 wt % to 99.9 wt % acetic acid.

2. The process of claim 1, wherein the dehydrating removes at least 15% of the water in the crude alkylenating agent stream.

3. The process of claim 1, wherein the dehydrating removes at least 30% of the water in the crude alkylenating agent stream.

4. The process of claim 1, wherein the dehydrating removes at most 5% of the alkylenating agent in the crude alkylenating agent stream.

5. The process of claim 1, wherein the crude alkylenating agent stream comprises at least 30 wt. % alkylenating agent and at least 20 wt. % water.

6. The process of claim 1, wherein the dehydrated alkylenating agent stream comprises at least 60 wt. % alkylenating agent.

7. The process of claim 1, wherein the crude alkylenating agent stream further comprises methanol.

8. The process of claim 1, wherein the dehydrating is achieved via at least one evaporator.

9. The process of claim 8, wherein the evaporator is operated at a pressure from 1 kPa to 80 kPa.

10. The process of claim 1, wherein the dehydrating is achieved via at least one distillation column.

11. The process of claim 10, wherein the at least one distillation column is operated at a pressure ranging from 450 kPa to 790 kPa.

12. The process of claim 10, wherein the at least one distillation column is operated at a condenser temperature ranging from 140° C. to 160° C.

13. The process of claim 1, wherein the conversion of alkylenating agent to acrylate product is at least 10%.

14. The process of claim 1, wherein acetic acid conversion based on acetic acid fed to the reactor is at least 10%.

15. The process of claim 1, wherein the space time yield of acrylates is between 25 to 500 grams/liter of catalyst/hour when the contacting is conducted at 370° C.

16. The process of claim 1, further comprising reacting at least a portion of the alkylenating agent stream with acetic acid to form acrylate product.

17. The process of claim 1, wherein the acetic acid is formed from methanol and carbon monoxide, wherein the methanol and the carbon monoxide are derived from syngas, and wherein the syngas is derived from a carbon source selected from the group consisting of natural gas, oil petroleum, coal, biomass, and combinations thereof.

18. A process for producing an acrylate product, comprising the steps of:
    reacting a dehydrated alkylenating agent stream comprising less than 35 wt % water with acetic acid from an acetic acid feed stream in a reactor to form a crude acrylate product stream comprising the acrylate product, an alkylenating agent and acetic acid;
    distilling at least a portion of the crude acrylate product stream to form an overhead comprising an alkylenating agent stream comprising at least 5 wt % alkylenating agent and a residue comprising an intermediate product stream comprising acrylate product and acetic acid; and
    separating the intermediate product stream to form a finished acrylate product stream comprising at least 85 wt % acrylic acid and a first finished acetic acid stream comprising from 50 wt % to 99.9 wt % acetic acid.

19. The process of claim 18, wherein the dehydrated alkylenating stream comprises more than 55 wt. % alkylenating agent.

20. The process of claim 18, further comprising dehydrating a crude alkylenating stream to form the dehydrated alkylenating stream.

21. The process of claim 20, wherein the crude alkylenating stream comprises at least 30 wt. % water.

22. The process of claim 20, wherein the dehydration occurs in at least one vacuum evaporator.

23. The process of claim 20, wherein the dehydration occurs in a series of vacuum evaporators.

24. The process of claim 20, wherein the dehydration is carried out at a pressure from 1 kPa to 80 kPa.

25. The process of claim 20, wherein at least 65 wt. % of water is removed from the crude alkylenating stream.

26. A process for producing an acrylate product, comprising the steps of:
    dehydrating a crude alkylenating stream to achieve at least 60 wt. % formaldehyde and less than 35 wt % water in the dehydrated stream;
    reacting the dehydrated alkylenating stream with acetic acid from an acetic acid feed stream in a reactor to form a crude acrylate product stream comprising the acrylate product, an alkylenating agent and acetic acid;
    distilling at least a portion of the crude acrylate product stream to form an overhead comprising an alkylenating agent stream comprising at least 5 wt % alkylenating agent and a residue comprising an intermediate product stream comprising acrylate product and acetic acid; and
    separating the intermediate product stream to form a finished acrylate product stream comprising at least 85 wt % acrylic acid and a first finished acetic acid stream comprising from 50 wt % to 99.9 wt % acetic acid.

27. The process of claim 26, wherein the dehydrating occurs in at least one evaporator.

28. The process of claim 26, wherein the dehydrating occurs in at least one distillation column.

29. A process for producing an acrylate product, comprising the steps of:
    dehydrating a crude alkylenating stream to remove at least 15% of the water therefrom;
    reacting the dehydrated alkylenating stream with acetic acid from an acetic acid feed stream in a reactor to form a crude acrylate product stream comprising the acrylate product, an alkylenating agent and acetic acid;
    distilling at least a portion of the crude acrylate product stream to form an overhead comprising an alkylenating agent stream comprising at least 5 wt % alkylenating agent and a residue comprising an intermediate product stream comprising acrylate product and acetic acid; and separating the intermediate product stream to form a finished acrylate product stream comprising at least 85 wt % acrylic acid and a first finished acetic acid stream comprising from 50 wt % to 99.9 wt % acetic acid.

* * * * *